US008043860B2

(12) United States Patent
Lefebvre et al.

(10) Patent No.: US 8,043,860 B2
(45) Date of Patent: *Oct. 25, 2011

(54) VAPOCHROMIC COORDINATION POLYMERS FOR USE IN ANALYTE DETECTION

(75) Inventors: Julie Lefebvre, Saint-Jean-sur-Richelieu (CA); Michael Iacov Katz, North Vancouver (CA); Daniel B. Leznoff, Vancouver (CA)

(73) Assignee: Simon Fraser University, Burnaby (CA)

( * ) Notice: Subject to any disclaimer, the term of this patent is extended or adjusted under 35 U.S.C. 154(b) by 60 days.

This patent is subject to a terminal disclaimer.

(21) Appl. No.: 12/169,406

(22) Filed: Jul. 8, 2008

(65) Prior Publication Data

US 2009/0130768 A1 May 21, 2009

Related U.S. Application Data

(63) Continuation-in-part of application No. 11/577,299, filed as application No. PCT/CA2005/001601 on Oct. 17, 2005.

(60) Provisional application No. 60/618,573, filed on Oct. 15, 2004.

(51) Int. Cl.
*G01N 21/00* (2006.01)
(52) U.S. Cl. ............... 436/164; 436/2; 436/80; 436/81; 436/126; 436/166; 436/167; 436/181; 436/183; 252/408.1
(58) Field of Classification Search .................. None
See application file for complete search history.

(56) References Cited

U.S. PATENT DOCUMENTS 4,826,774 A  5/1989  Nagel
(Continued)

FOREIGN PATENT DOCUMENTS

EP   0277033 B1   4/1994
(Continued)

OTHER PUBLICATIONS

Stender, Matthias, et al. New Structural Features of Unsupported Chains of Metal Ions in Luminescent [(NH3)4Pt][Au(CN)2]2.1. 5(H2O) and Related Salts, 2003, Inorgainc Chemistry, vol. 42(15), p. 4504-4506.*

(Continued)

*Primary Examiner* — Yelena G Gakh
*Assistant Examiner* — Robert Xu
(74) *Attorney, Agent, or Firm* — Oyen Wiggs Green & Mutala LLP

(57) ABSTRACT

This application relates to vaprochromic coordination polymers useful for analyte detection. The vapochromism may be observed by visible color changes, changes in luminescence, and/or spectroscopic changes in the infrared (IR) signature. One or more of the above chromatic changes may be relied upon to identify a specific analyte, such as a volatile organic compound or a gas. The chromatic changes may be reversible to allow for successive analysis of different analytes using the same polymer. The polymer has the general formula $M_W[M^-_X(Z)_Y]_N$ wherein M and $M^-$ are the same or different metals capable of forming a coordinate complex with the Z moiety; Z is selected from the group consisting of halides, pseudohalides, thiolates, alkoxides and amides; W is between 1-6; X and Y are between 1-9; and N is between 1-5. Optionally, an organic ligand may be bound to M. In alternative embodiments of the invention M may be a transition metal, such as Cu and Zn. $M^-$ may be a metal such as Au, Ag, Hg and Cu, and Z may be a pseuodohalide, such as CN, SCN, SeCN, TeCN, OCN, CNO and NNN. In one particular embodiment a new class of [Metal(CN)$_2$]-based coordination polymers with vapochromic properties is described, such as Cu[Au(CN)$_2$]$_2$ and Zn[Au(CN)$_2$]$_2$ polymers.

25 Claims, 18 Drawing Sheets

The extended 1-D zig-zag chain structure of Cu[Au(CN)$_2$]$_2$(DMSO)$_2$ (1).
DMSO-methyl groups were removed for clarity.

U.S. PATENT DOCUMENTS

| | | | |
|---|---|---|---|
| 4,834,909 | A | 5/1989 | Nagel |
| 5,766,952 | A | 6/1998 | Mann et al. |
| 2008/0071053 | A1 | 3/2008 | Lefebvre et al. |

FOREIGN PATENT DOCUMENTS

| | | |
|---|---|---|
| ES | 2151424 B1 | 7/2001 |

OTHER PUBLICATIONS

N. Blom et al., Thallium Dicyanoaurate(I), Tl[AU(CN)2], and Cesium Dicyanoaurate(I), Cs[Au(CN)2], Acta Cryst., C40, 1984, 1767-1769.

Angeline Stier & Klaus-Jurgen Range, Dicyanometallate, VII[1] Preparation and Crystal Structure of Gadolinium-tris-dicyanoaurate (I), Gd [Au(CN)2]3.2,3H20, Z. Naturforsch, 51b, 1996, 698-702.

J. Chomic et al., Thermal Properties of Complexes M(NH3)2[Ag(CN)2]2 (M(II) = Ni, Cu, Cd, Chem. Papers 47(3), 1993, 175-178.

Bernard F. Hoskins et al., Six Interpenetrating Quartz-Like Nets in the Structure of ZnAu2(CN)4, Angew Chem. Int. Ed. Engl., 34, No. 11, 1995, 1203-1204.

C. Bariain et al., Detection of volatile organic compound vapors by using a vapochromic material on a tapered optical filter, Applied Physics Letters, vol. 77, No. 15, Oct. 9, 2000, 2274-2276.

Enrique Colacio et al., Aurophilicity as a cofactor in crystal engineering. Dicyanoarate(I) anion as a building block in a novel Co(II)-Au(I) bimetallic assembly, ChemComm, 2002, 592-593.

Takayoshi Soma and Toshitake Iwamoto, A Three-Dimensional Warp-and-Woof Structure Interwoven by a Couple of Two-Dimensional Network Layers in the Crystal Structure of [trans-Cd(NH3)2{Ag(CN)2}2]n, Chemistry Letters, 1995, 271-272.

Christopher L. Exstrom et al., Inclusion of Organic Vapors by Crystalline, Solvatochromic [Pt(aryl isonitrile)4][Pd(CN)4] Compounds, Chem. Mater., 7, 1995, 15-17.

Charles A. Daws et al., "Vapochromic" Compounds as Environmental Sensors. 2. Synthesis and Near-Infrared and Infrared Spectroscopy Studies of [Pt(arylisocyanide)4][Pt(CN)4] upon Exposure to Volatile Organic Compound Vapors, Chem. Mater., 9, 1997, 363-368.

Christopher L. Exstrom et al., Infrared spectroscopy studies of platinum salts containing Tetracyanoplatinate(II). Evidence for strong hydrogen-bonding interactions in "Vapochromic" environmental sensor materirals, Chem. Mater., 10, 1998, 942-945.

Yoshihito Kunugi et al., A Vapochromic Photodiode, Chem. Mater., 10, 1998, 1487-1489.

Wen Dong et al., 3D porous and 3D interpenetrating triple framework structures constructed by aurophilicity-coordination interplay in {Mn[Au{CN)2]2(H2O)2}n and {KFe[Au(CN)2]3}n, ChemComm, 2003, 2544-2545.

Zerihun Assefa et al., Photoluminescence Studies of Lanthanide Ion Complexes of Gold and Silver Dicyanides: A New Low-Dimensional Solid State Class for Nonradiative Excited-State Energy Transfer, Inorganic Chemistry, 33, 1994, 2187-2195.

Eduardo J. Fernandez et al., A Detailed Study of the Vapochromic Behavior of {Tl{Au(C6Cl5)2]}n, Inorganic Chemistry, 43, 2004, 3573-3581.

Zerihun Assefa and Howard H. Patterson, Photoluminescence Studies of Lanthanide Ion Complexes of Gold and Silver Dicyanides. 2. A New Low Dimensional Solid State Class for Nonradiative Excited State Energy Transfer, Inorganic Chemistry, 33, 1994, 6194-6200.

W. B. Feldtmann, Gold-Zinc-Cyanide, The Journal of the Chemical, Metallurgical and Mining Society of South Africa, vol. XX Aug. 1919. No. 2, 13-14.

Carrie E. Buss and Kent R. Mann, Synthesis and Characterization of Pt(CN-p-(C2H5)C6H4)2(CN)2, a Crystalline Vapoluminescent Compound That Detects Vapor-Phase Aromatic Hydrocarbons, J. Am. Chem. Soc., vol. 124, No. 6, 2002, 1031-1039.

M. Adnan Mansour et al., Linear Chain Au{I} Dimer Compounds as Environmental Sensors: A Luminescent Switch for the Defection of Volatile Organic Compounds, J. Am. Chem. Soc., 120, 1998, 1329-1330.

Eduardo J. Fernandez et al., {Tl[Au(C6C15)2]}n: A Vapochromic Complex, J. Am. Chem. Soc., vol. 125, No. 8, 2003, 2022-2023.

Rochelle L. White-Morris et al., Remarkable Variations in the Luminescence of Frozen Solutions of [Au{C(NHMe)2}2] (PF6).0.5(Acetone). Structural and spectroscopic studies of the effects of anions and solvents on gold (I) carbene complexes, J. Am. Chem. Soc., vol. 124, No. 10, 2002, 2327-2336.

Laurance G. Beauvais et al., Cyano-Bridged Re6Q8 (Q=S, Se) Cluster-Cobalt(II) Framework Materials: Versatile Solid Chemical Sensors, J. Am. Chem. Soc., vol. 122, No. 12, 2000, 2763-2772.

Carrie E. Buss et al., Structural Investigations of Vapochromic Behavior. X-ray Single-Crystal and Powder Diffraction Studies of [Pt(CN-iso-C3H7)4][M(CN)4] for M = Pt or Pd, J. Am. Chem. Soc., vol. 120, No. 31, 1998, 7783-7790.

Steven M. Drew et al., An Electronic Nose Transducer Array of Vapoluminescent Platinum(II) Double Salts, J. Am. Chem. Soc., vol. 123, No. 34, 2001, 8414-8415.

Manal A. Rawashdeh-Omary et al., Chemistry and Optoelectronic Properties of Stacked Supramolecular Entities of Trinuclear Gold(I) Complexes Sandwiching Small Organic Acids, J. Am. Chem. Soc., vol. 123, No. 39, 2001, 9689-9691.

S.C. Abrahams et al., Piezoelectric KCo[Au(CN)2]3: Room temperature crystal structure of a cobalt-hardened gold electrodeposition process component, J. Chem. Phys., 73(9), 1980, 4585-4590.

S.C. Abrahams et al., Cobalt cyanoaurate: Crystal structure of a component from cobalt-hardened gold electroplating baths, J. Chem. Phys., 76(11), 1982, 5458-5462.

Daniel B. Leznoff et al., An aurophilicity-determined 3-D bimetallic coordination polymer: using [Au(CN)2]-to increase structural dimensionality through gold . . . gold bonds in (tmeda)Cu[Au(CN)2]2, Chem Comm, 2001, 259-260.

Daniel B. Leznoff et al., Gold-Gold Interactions as Crystal Engineering Design Elements in Heterobimetallic Coordination Polymers, Inorganic Chemistry, vol. 40, No. 23, 2001, 6026-6034.

Yoshihito Kunugi et al., A Vapochromic LED, J. Am. Chem. Soc., vol. 120, No. 3, 1998, 589-590.

Zerihun Assefa et al., Europium (III) Tris [dicyanoargentate (I)] Trihydrate, Eu [Ag (CN) 2] 3.3 H2O, Acta Cryst., C51, 1995, 2527-2529.

Wei Han et al., Synthesis and Characterisation of Two Supramolecular Polymers [CuAg4 (CN) 6 (tacn)] n and [CuAu2 (CN) 4 (tacn)] n Containing Metal-Metal Interactions, European Journal of Inorganic Chemistry, 10, 2004, 2130-2136.

* cited by examiner

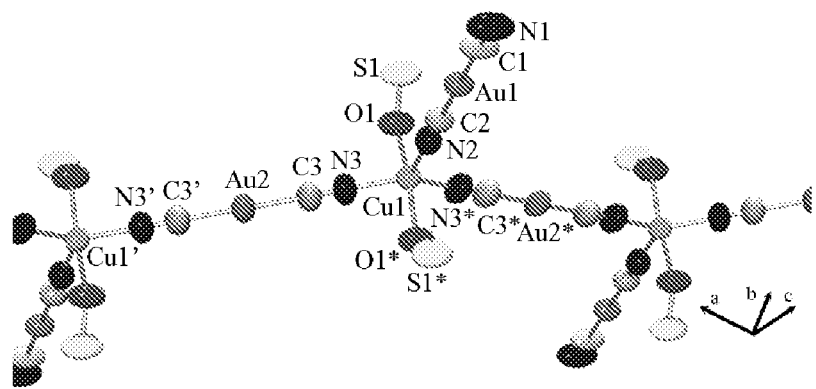
Figure 1. The extended 1-D zig-zag chain structure of Cu[Au(CN)$_2$]$_2$(DMSO)$_2$ (1). DMSO-methyl groups were removed for clarity.

(a)
(b)
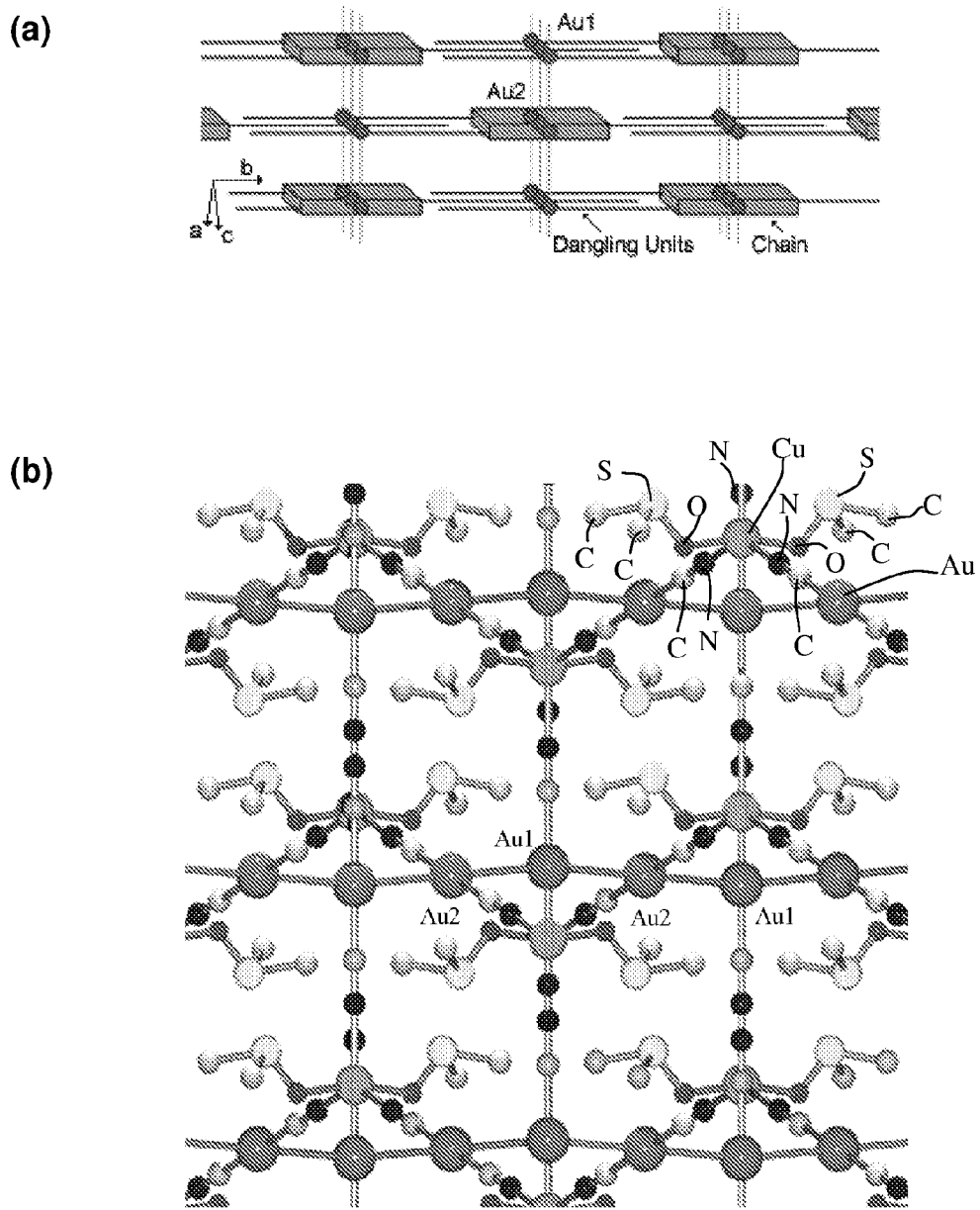
Figure 2. (a): Offset stacks of chains in 1, viewed down the (101)-plane (slightly tilted). Au-Au bonds connect bridging and dangling [Au(CN)$_2$]$^-$ units of neighboring chains (vertical lines). (b): 3-D structure of 1 formed via Au-Au bonding, viewed down the $a$-axis.

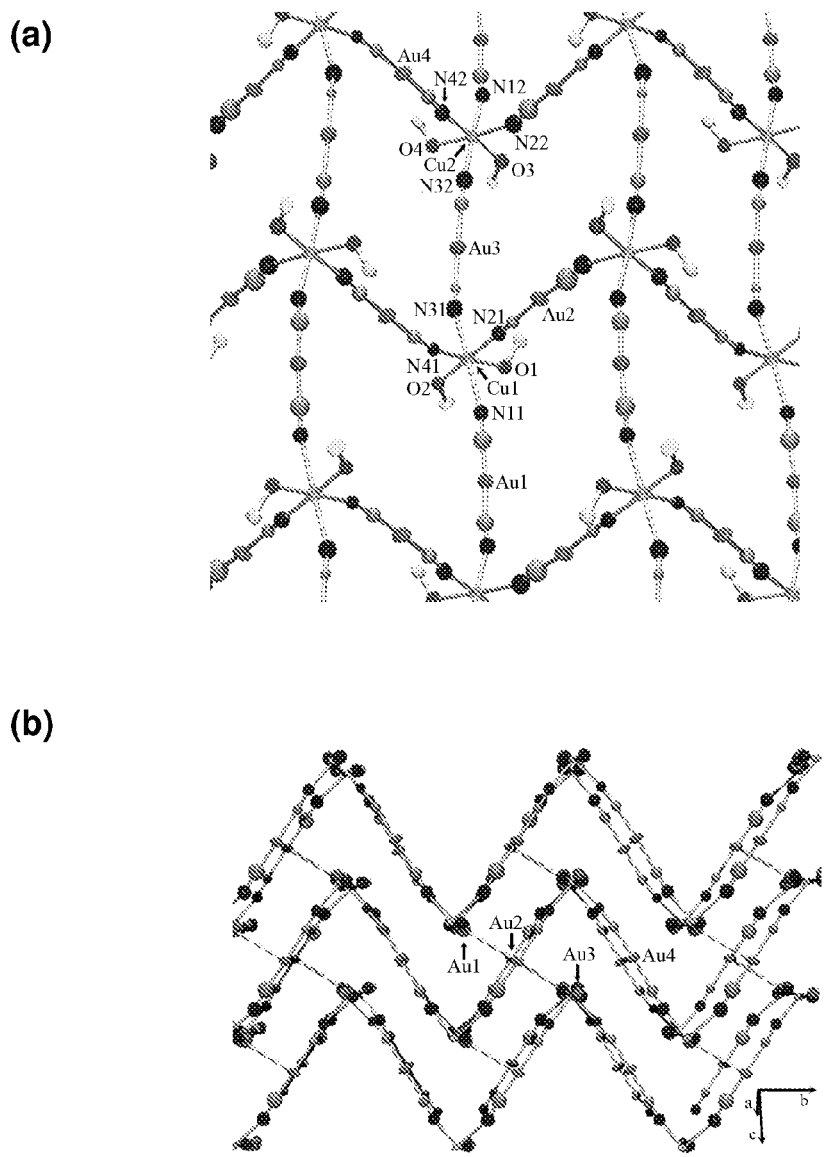
Figure 3. (a): Extended structure of 2 showing the 2-D corrugated layers, viewed down the *a*-axis. DMSO-methyl groups were removed for clarity. (b): Layers stacked via aurophilic interactions to yield a 3-D network.

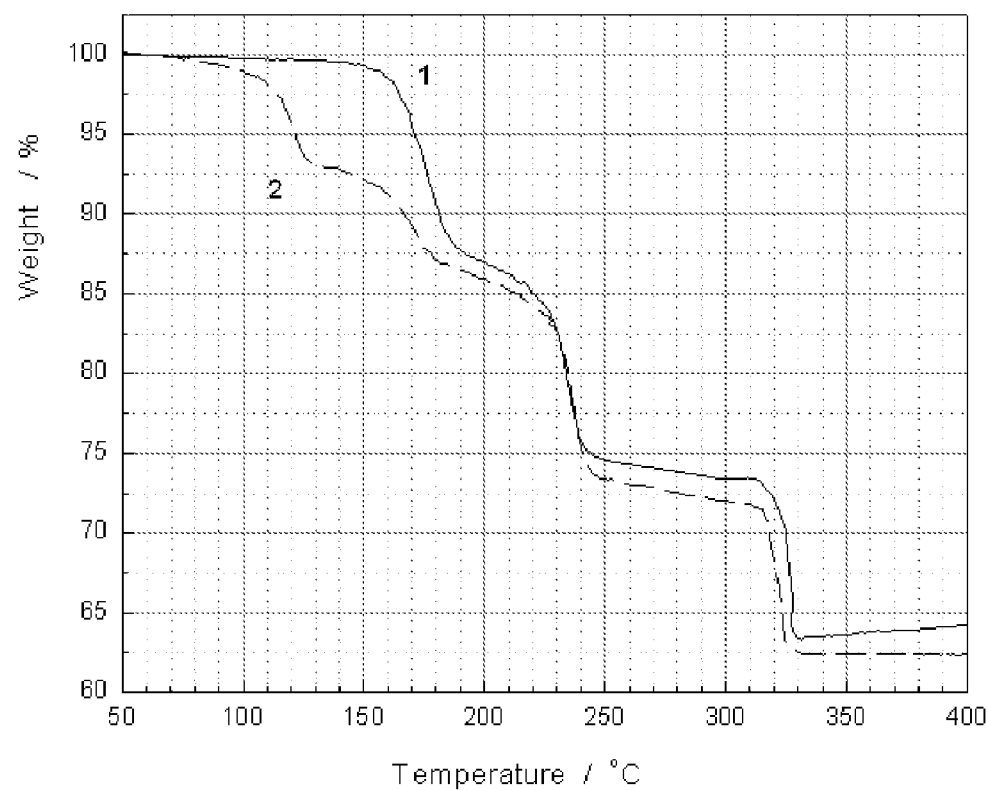
Figure 4. Thermal decomposition of polymorphs 1 and 2.

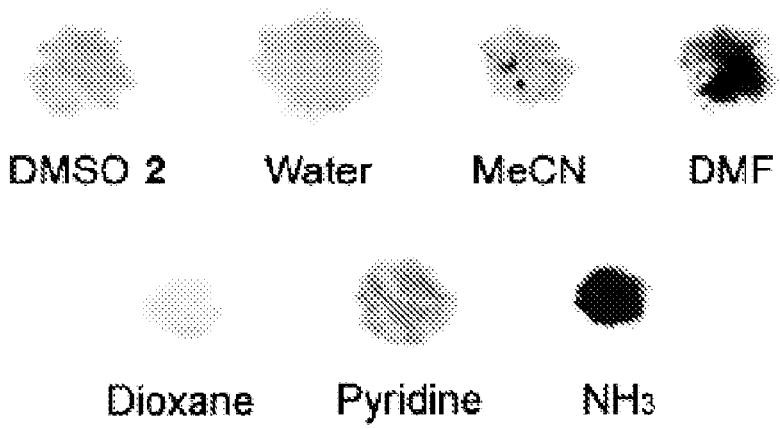
Figure 5. Powder sample of 2 exposed to various solvent vapours.

(a)
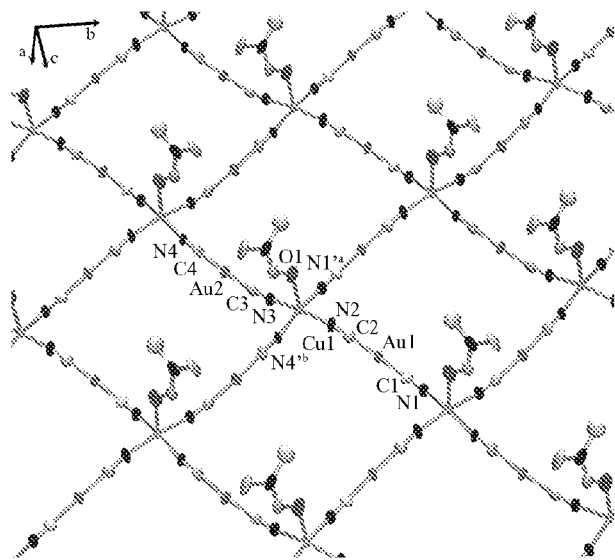
(b)
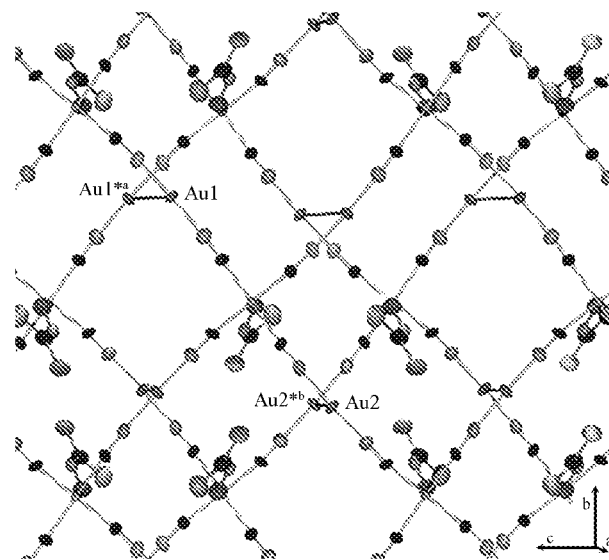
Figure 6. (a): Extended structure of 3 showing the 2-D layers (hydrogen atoms were removed for clarity). (b): Aurophilic interactions between the layers yield a 3-D network.

(a)
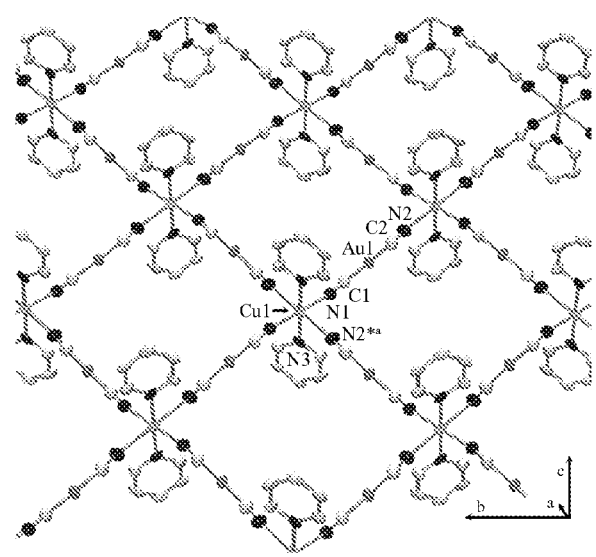
(b)
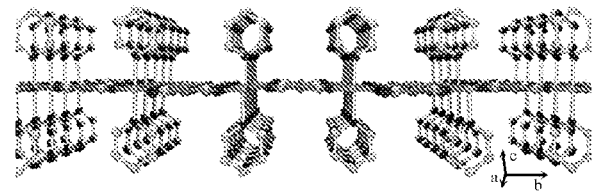
Figure 7. (a): Extended structure of 4 showing a 2-D layer. (b): Side view of a 2-D layer showing the pyridine ligands situated above and below the plane.

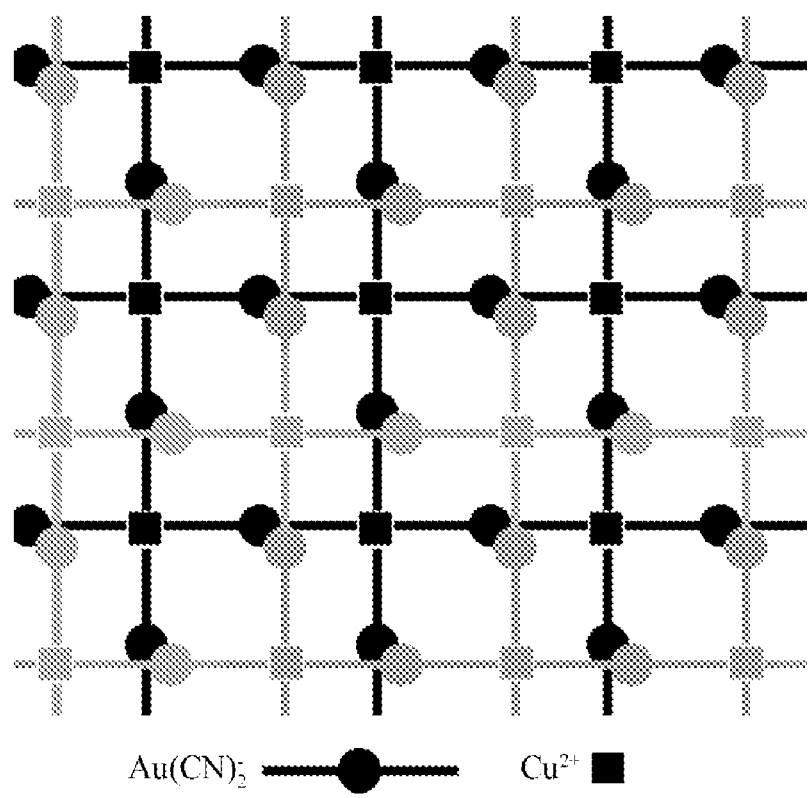
Figure 8. Postulated 2-D square grid structure of Cu[Au(CN)$_2$]$_2$.

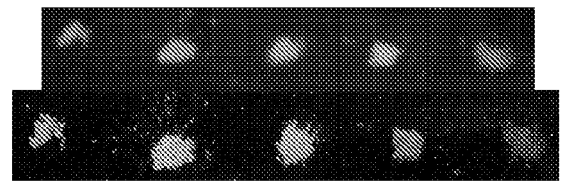
Figure 9. Changes in luminescence in the $Zn[Au(CN)_2]_2(analyte)_x$ system (top - under room light; bottom - under UV light). From left to right: Analyte = None, $NH_3$, pyridine, $CO_2$, DMSO. The cyanide-IR changes are dramatic and distinctive for each analyte.

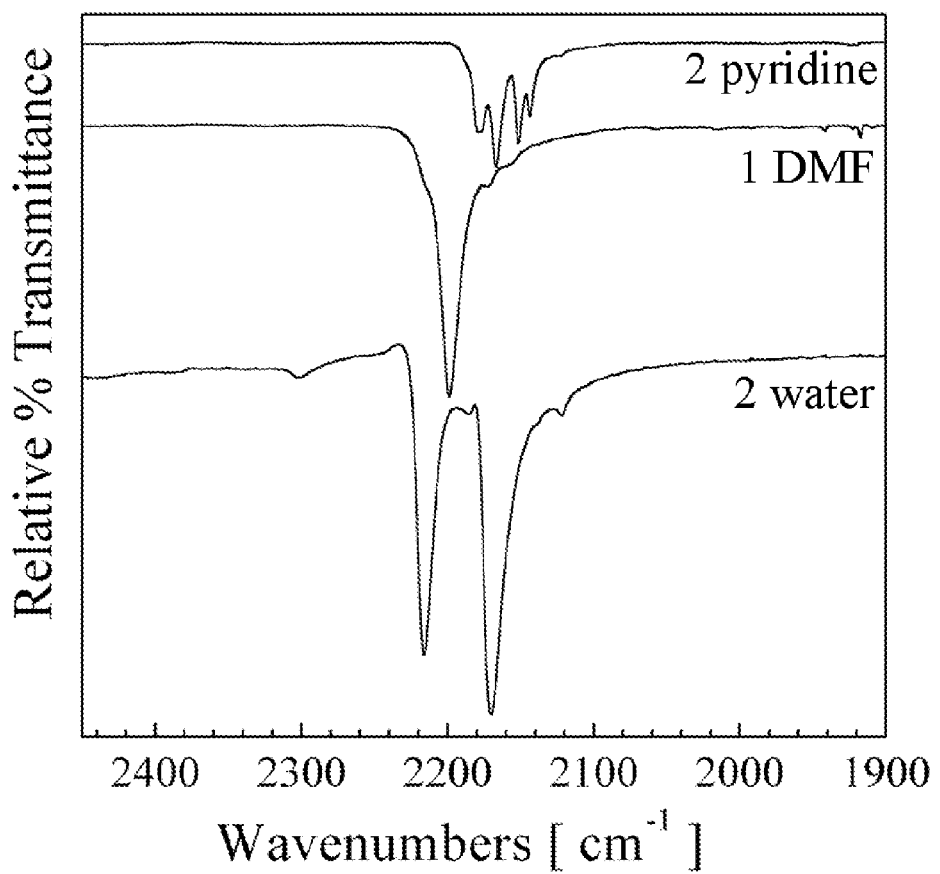
Figure 10. Spectrograph showing the comparative IR spectra in the cyanide region for the three analytes: pyridine, DMF and water.

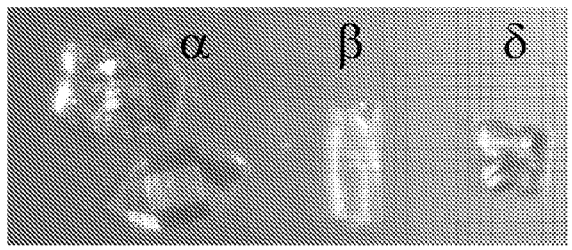

Figure 11: Crystal habit of polymorph crystals. (Left): Two hexagonal crystal habits of 13α.(Middle): Plate shaped crystal habit of 13β. (Right): Cross shaped crystal habit of 13γ; Each arm of the cross is a two component non-merohedral twin.

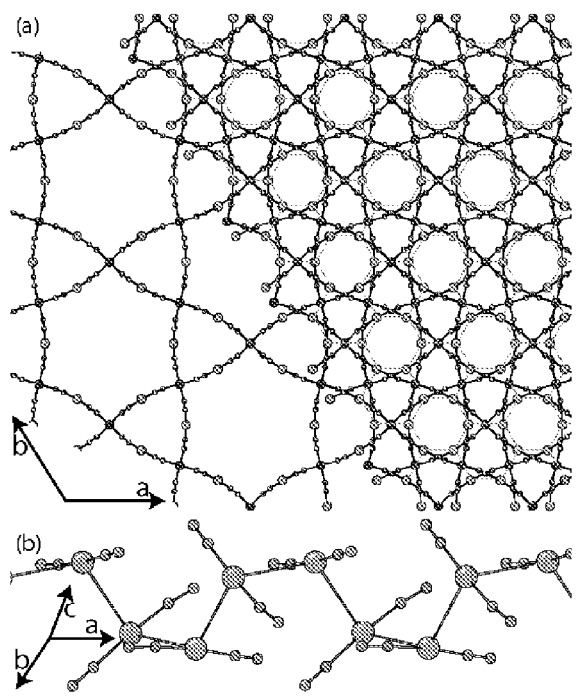

Figure 12: (a) Crystal structure of 13α viewed down the c-axis. (Left): A single quartz-like network. (Right): All six interpenetrated quartz-like networks. (b) 1-D chain of gold-gold bonded $Au(CN)_2^-$ units.

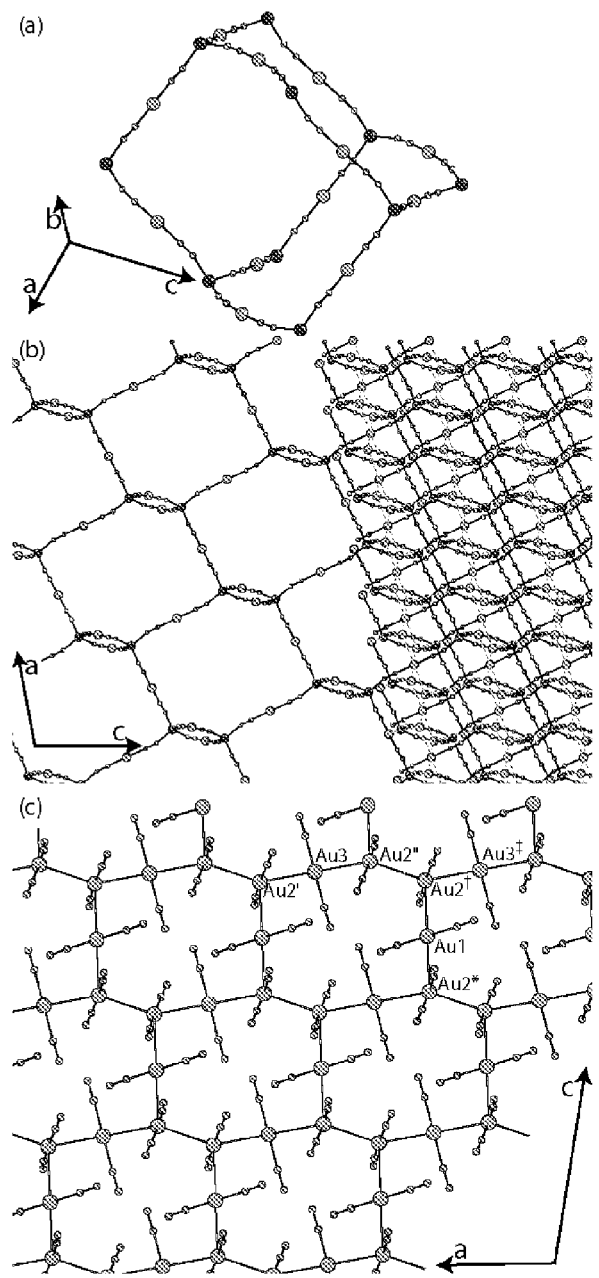
Figure 13: Crystal structure of 13β. (a) Single diamond-like repeat unit. (b) Left: A single diamond-like network viewed down the b-axis. (Right): All 5 interpenetrated networks. (c) Distorted Hexagonal 2-D (6,3) network of gold-gold bonded Au(CN)$_2^-$ units.

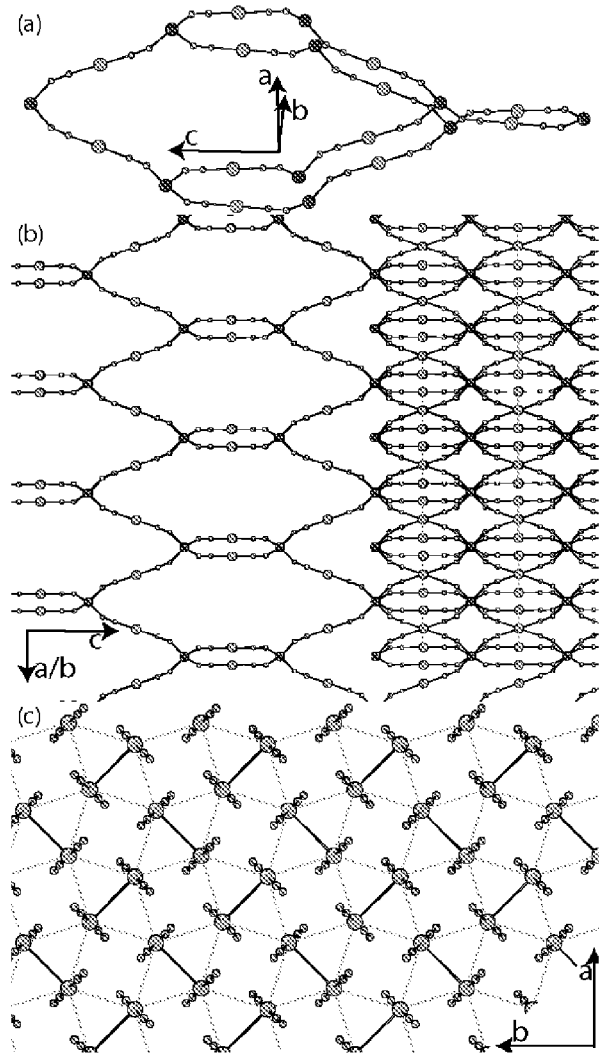
Figure 14: Crystal structure of 13γ. (a) Single diamond-like repeat unit. (b) Left: Single diamondlike framework. Right: All 4 interpenetrated networks. (c) network gold-gold bonded Au(CN)$_2^-$ units containing dimers of Au(CN)$_2^-$ (Au-Au = 3.29 Å) connected via longer Au-Au distances of 3.58 Å.

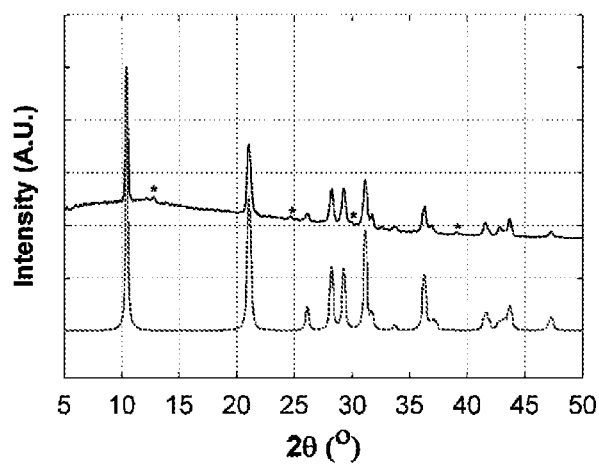
Figure 15: Simulated (lower) and observed (upper) powder difractograms of 13γ. Peaks labelled with * are due to a small (3 %) percentage of 13α impurity.

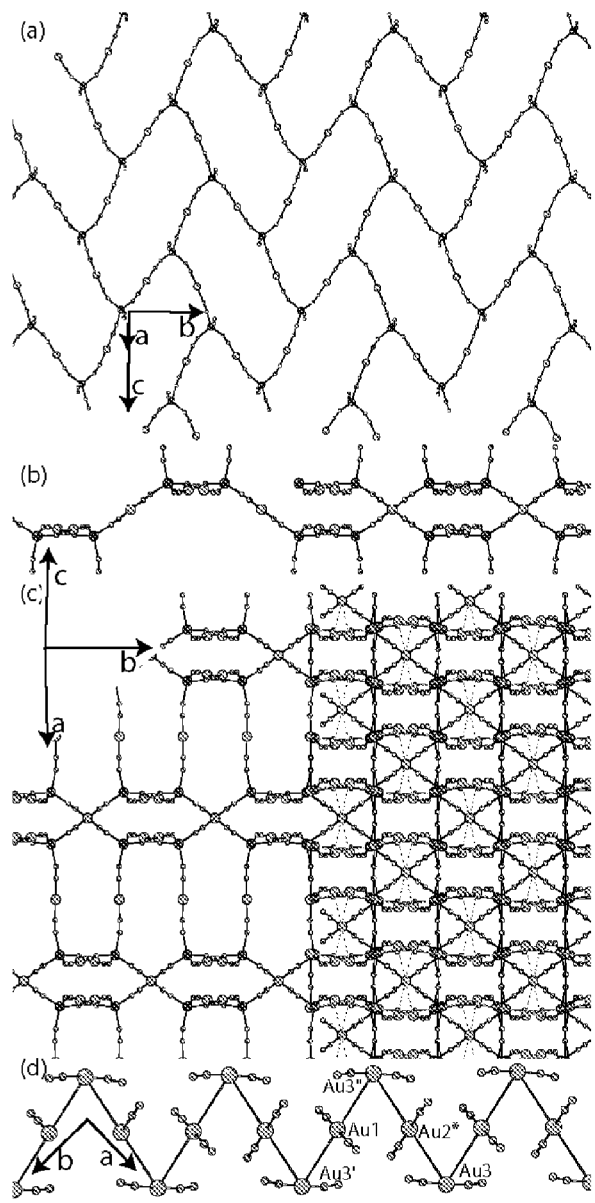
Figure 16: Crystal structure of 13δ. (a) One herringbone network. (b) Left: Side view of herringbone network. Right: pair of interwoven herringbone networks. (c) Left: One full 3-D network. Right: All 3 interpenetrated networks. (d) 1-D chain of gold-gold bonded $Au(CN)_2^-$ units.

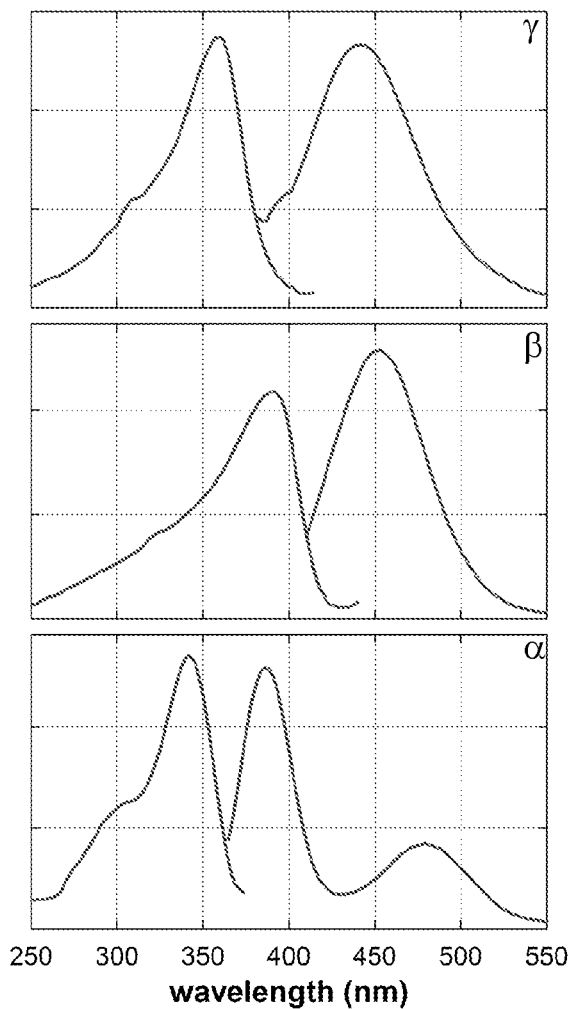
Figure 17: Excitation (left) and emission (right) spectra of 13α (bottom) 13β, (middle) 13γ, and (top).

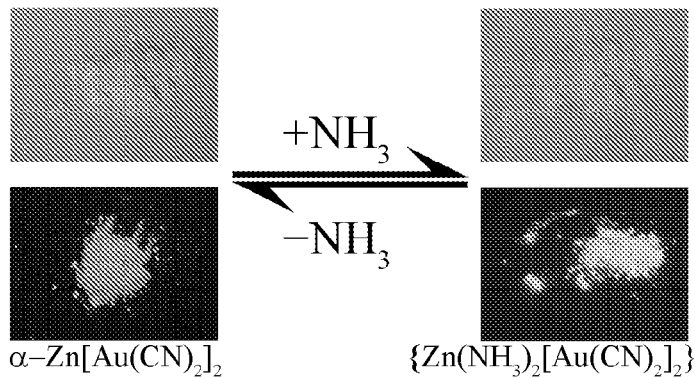
Figure 18: Powder of 13α (Left) under UV and Visible light (bottom and top respectively). After exposure to ammonia a yellow compound of {Zn(NH$_3$)$_2$[Au(CN)$_2$]$_2$} 14 remains (top right) with bright green luminescence (bottom right).
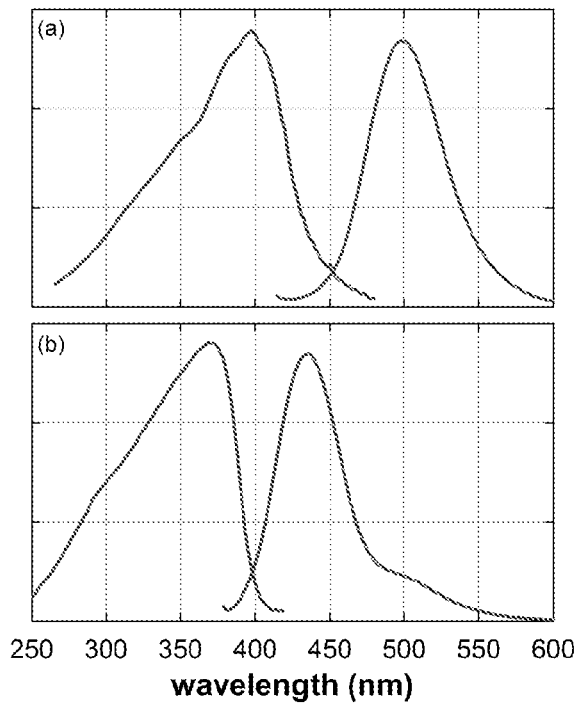
Figure 19: Excitation and emission spectrum of (a) {Zn(NH$_3$)$_2$[Au(CN)$_2$]$_2$} 14 and (b) fully saturated {Zn(NH$_3$)$_4$][Au(CN)$_2$]$_2$} 15.

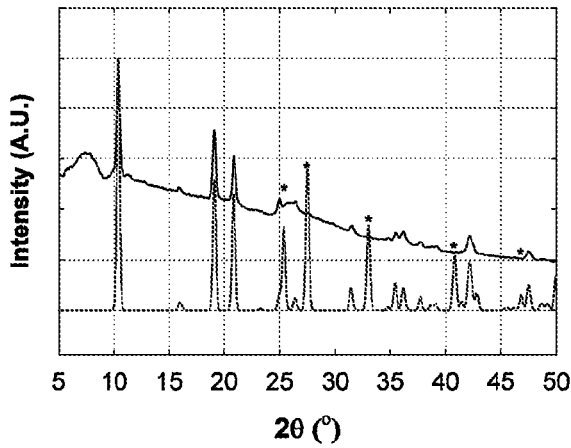
Figure 20: Simulated (lower) and observed (upper) powder difractograms of {Zn(NH$_3$)$_2$[Au(CN)$_2$]$_2$} 14. The 21*l* reflections are labeled with a *.
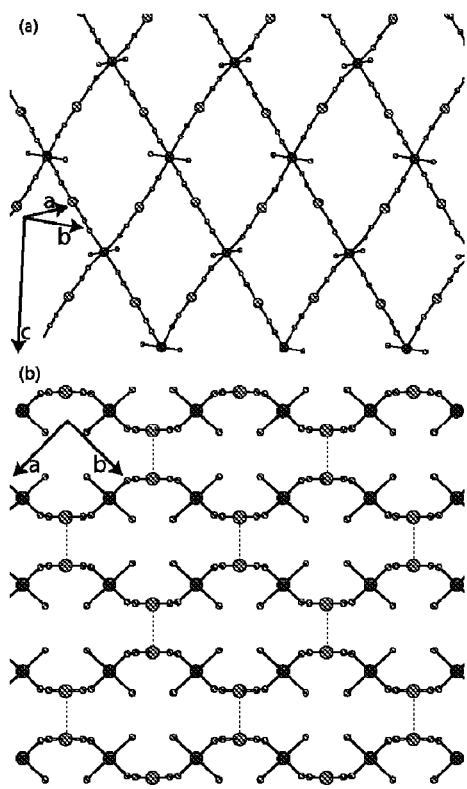
Figure 21: Crystal structure of {Zn(NH$_3$)$_2$[Au(CN)$_2$]$_2$} 14. (a) Corrugated sheet of {Zn(NH$_3$)$_2$[Au(CN)$_2$]$_2$} 14. (b) Side view of stacked sheets in {Zn(NH$_3$)$_2$[Au(CN)$_2$]$_2$} 14.

VAPOCHROMIC COORDINATION POLYMERS FOR USE IN ANALYTE DETECTION

REFERENCE TO RELATED APPLICATIONS

This application claims the benefit of U.S. provisional patent application Ser. No. 60/618,573 filed 15 Oct. 2004 which is hereby incorporated by reference.

This application is a continuation-in-part of pending U.S. patent application Ser. No. 11/577,299 filed 17 Oct. 2005 which is hereby incorporated by reference.

FIELD OF THE INVENTION

This application relates to coordination polymers having vapochromic properties useful for analyte detection.

BACKGROUND OF THE INVENTION

The controlled design and synthesis of metal-organic coordination polymers from the self-assembly of simple molecular building blocks is of intense interest due to the promise of generating functional materials.[1, 2] Vapochromic materials, which display optical absorption or luminescence changes upon exposure to vapors of analytes, such as volatile organic compounds (VOCs), have been a focus of attention due to their potential applications as chemical sensors.[3-9] For example, when exposed to certain organic solvents, the extended Prussian Blue $Co^{2+}$—$[Re_6Q_8(CN)_6]^{4-}$ (Q=S, Se) system yields dramatic changes in the visible spectrum that are attributable to the sensed solvent impacting the geometry and hydration around the $Co^{11}$ centers.[9]

Several vapochromic compounds based on $Au^I$, $Pd^{II}$, and $Pt^{II}$ coordination polymers have also been reported.[3-8] The vapochromism in these systems is based on changes in both the visible absorption and emission spectra. In the linear $\{Tl[Au(C_6Cl_5)_2]\}_n$ polymer, weak interactions between the Tl atoms and the adsorbed VOC molecules modify slightly the color, and more significantly the emission spectra.[6] On the other hand, changes in the emission spectra of $[Pt(CN-R)_4]$ $[M(CN)_4]$ (R=iso-$C_3H_7$ or $C_6H_4$—$C_nH_{2n+1}$; n=6, 10, 12, 14 and M=Pt, Pd) occur when metal-metal distances are modified due to the presence of VOC molecules in lattice voids; small changes in the absorption spectrum can also be observed.[7, 10] Another example is the trinuclear $Au^I$ complex with carbeniate bridging ligands, for which its luminescence is quenched in the solid-state when $C_6F_6$ vapor is adsorbed due to the disruption of Au—Au interactions.[5]

Some of these vapochromic materials have recently been incorporated in chemical sensor devices. For example, [Au—$(PPh_2C(CSSAuC_6F_5)PPh_2Me)_2][ClO_4]$ has been used in the development of an optical fiber volatile organic compound sensor.[11] A vapochromic light emitting diode[12] and a vapochromic photodiode[13] have also been built using tetrakis(p-dodecylphenylisocyano) platinum tetranitroplatinate and bis (cyanide)-bis(p-dodecylphenylisocyanide)platinum(II), respectively.

In these previous discoveries, slight shifts in the $\upsilon_{CN}$ stretch are observed if hydrogen-bonding between the N(cyano) atoms and the VOC molecules present in the lattice occurs. Importantly, VOCs cannot be readily differentiated or identified via IR spectroscopy in this case since $\upsilon_{CN}$ shifts of only 0-10 cm$^{-1}$ are usually observed.[11, 14, 15]

To overcome the shortcomings of the prior art, the need has arisen for coordination polymers having improved vapochromic properties for enhancing the sensitivity of analyte detection. The IR signatures achieved by the present invention are unusually diagnostic for a particular analyte, both in the number and position of the IR bands. In the case of some gases, the adsorption of the analyte to the polymer substantially enhances the IR response. That is, the response in the $\upsilon_{CN}$ or other pertinent region of the spectrum is extremely strong compared to the direct IR-signature of some gases, which is the current state-of-the-art in gas sensors. Moreover, in the present invention the vapochromism of polymers can be readily and reversibly observed both by multiple means, such as visible colour changes and luminescence changes in addition to IR spectroscopic changes.

SUMMARY OF THE INVENTION

In accordance with the invention, a vapochromic polymer is described having the general formula $M_W[M^-_X(Z)_Y]_N$ wherein M and M$^-$ are the same or different metals capable of forming a coordinate complex with the Z moiety; Z is selected from the group consisting of halides, pseudohalides, thiolates, alkoxides and amides; W is between 1-6; X and Y are between 1-9; and N is between 1-5. For example, in one embodiment W and X are 1 and Y and N are 2.

The vapochromic properties of the polymer change when the polymer is exposed to different analytes. The polymer may therefore be used for analyte detection. The vapochromism may be observed by visible color changes, changes in luminescence, and/or spectroscopic changes in the infrared IR signature. One or more of the above chromatic changes may be relied upon to identify a specific analyte, such as a volatile organic compound or a gas. The chromatic changes may be reversible to allow for successive analysis of different analytes using the same polymer.

In alternative embodiments of the invention M may be a transition metal, such as Cu and Zn. M$^-$ may be a metal such as Au, Ag, Hg and Cu, and Z may be a pseuodohalide, such as CN, SCN, SeCN, TeCN, OCN, CNO and NNN. Optionally, an organic ligand may be bound to M. In one particular embodiment a new class of [Metal(CN)$_2$]-based coordination polymers with vapochromic properties is described, such as Cu[Au(CN)$_2$]$_2$ and Zn[Au(CN)$_2$]$_2$ polymers.

BRIEF DESCRIPTION OF THE DRAWINGS

In drawings which describe embodiments of the invention but which should not be construed as restricting the spirit or scope of the invention in any way.

FIG. 1 is a diagram of the 1-D crystal structure of a first polymorph of Cu[Au(CN)$_2$]$_2$(DMSO). DMSO-methyl groups were removed for clarity.

FIGS. 2(a) and (b) are diagrams of the 3-D crystal structure of the first polymorph of Cu[Au(CN)$_2$]$_2$(DMSO)$_2$.

FIGS. 3(a) and (b) are diagrams of the 2-D and 3-D crystal structure of a second polymorph of Cu[Au(CN)$_2$]$_2$(DMSO)$_2$.

FIG. 4 is a graph showing the thermal stability of the first and second polymorphs of Cu[Au(CN)$_2$]$_2$(DMSO)$_2$.

FIG. 5 are photographs showing the vapochromic behavior of the second polymorph of Cu[Au(CN)$_2$]$_2$(DMSO)$_2$ after exposure to various analytes, namely DMSO, water, MeCN, DMF, Dioxane, Pyridine and NH$_3$.

FIGS. 6(a) and (b) are diagrams of the 2-D and 3-D crystal structure of Cu[Au(CN)$_2$]$_2$(DMF).

FIGS. 7(a) and (b) are diagrams of the 2D crystal structure of Cu[Au(CN)$_2$]$_2$(pyridine)$_2$.

FIG. 8 is a diagram of the postulated 2-D crystal structure of a solvent free complex of Cu[Au(CN)$_2$]$_2$.

FIG. 9 are photographs showing changes in luminescence in the $Zn[Au(CN)_2]_2(analyte)_N$ system (top—under room light; bottom—under UV light). From left to right: Analyte=None, $NH_3$, pyridine, $CO_2$, DMSO.

FIG. 10 is a spectrograph showing the comparative IR spectra in the cyanide region for three analytes (solvents), namely pyridine, DMF and water using the $Cu[Au(CN)_2]_2$ $(solvent)_X$ polymer.

FIG. 11 is a series of photographs showing the structure of $Zn[Au(CN)_2]_2$ polymorph crystals.

FIGS. 12(a) and 12(b) are diagrams of the crystal structure of an α polymorph of $Zn[Au(CN)_2]_2$.

FIGS. 13(a), 13(b) and 13(c) are diagrams of the crystal structure of an β polymorph of $Zn[Au(CN)_2]_2$.

FIGS. 14(a), 14(b) and 14(c) are diagrams of the crystal structure of an γ polymorph of $Zn[Au(CN)_2]_2$.

FIG. 15 is a graph showing a difractogram of the γ polymorph of $Zn[Au(CN)_2]_2$.

FIGS. 16(a), 16(b), 16(c) and 16(d) are diagrams of the crystal structure of an δ polymorph of $Zn[Au(CN_2]_2$.

FIG. 17 is a series of graphs showing excitation spectra for the α, β, and γ polymorphs of $Zn[Au(CN)_2]_2$.

FIG. 18 is a series of photographs of powder of the α polymorph of $Zn[Au(CN)_2]_2$ under UV and visible light before and after exposure to ammonia.

FIGS. 19(a) and 19(b) are graphs showing excitation and emission spectra of (a) $\{Zn(NH_3)_2[Au(CN)_2]_2\}$ and (b) fully saturated $\{Zn(NH_3)_4[Au(CN)_2]_2\}$.

FIG. 20 is a graph showing simulated and observed powder difractograms of $\{Zn(NH_3)_2[Au(CN)_2]_2\}$.

FIGS. 21(a) and 21(b) are diagrams of the crystal structure of $\{Zn(NH_3)_2[Au(CN)_2]_2\}$.

DETAILED DESCRIPTION OF THE INVENTION

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive, sense.

This application relates to vapochromic polymers useful for detection of analytes. The polymers have the general formula $M_W[M^-_X(Z)_Y]_N$ wherein M and $M^-$ are the same or different metals capable of forming a coordinate complex in conjunction with the Z moiety; Z is selected from the group consisting of halides, pseudohalides, thiolates, alkoxides and amides; W is between 1-6; X and Y are between 1-9; and N is between 1-5. As will be apparent to a person skilled in the art and as described herein, the vapochromic polymers of the invention may also comprise other constituents including ligands, counterbalancing ions and other metals. The invention encompasses polymers having the same empirical formula as set out above which exhibit vapochromic properties.

As described below, the vapochromism of the polymers may be observed by (1) visible changes, such as changes in colour or luminescence upon exposure to analytes, or by (2) infrared (IR) spectroscopic changes. The invention thus provides two means or "channels" to thereby achieve highly sensitive analyte detection. As used in this patent application the term "vapochromic" refers to a material that has a spectroscopic property change upon exposure to a liquid or the vapour of a volatile liquid or gas and the term vapochromism refers to such a spectroscopic property change. The spectroscopic property may include any wavelength of light including microwaves, infrared, visible colour and luminescence. As used in this patent application the process of "detecting chromatic changes" includes detecting a spectroscopic property change, including both visible and non-visible changes resulting from exposure to an analyte.

As exemplified by the examples described below, in some embodiments of the invention M is a transition metal such as copper (Cu) or zinc (Zn) and $M^-$ is a metal such as gold (Au), silver (Ag), mercury (Hg) or copper. The Z moiety may be an ion or anionic ligand. Suitable Z moieties include pseudohalide ions such as CN—. As will be apparent to a person skilled in the art, other suitable pseudohaldides include SCN, SeCN, TeCN, OCN, CNO and NNN. In particular embodiments of the invention $Cu[Au(CN)_2]_2$ and $Zn[Au(CN)_2]_2$ polymers are described. The $Cu[Au(CN)_2]_2$ embodiment takes advantage of the unique chemical properties of gold (I) and copper (II) ions, such as attractive gold-gold interactions and luminescence for gold and a flexible coordination sphere for copper. The attractive interactions enable the formation of chemically stable, high-dimensionality materials and the gold-luminescence, cyanide-IR and copper(II) visible spectrum can all act as simultaneous sensory outputs. Similarly, with respect to the $Zn[Au(CN)_2]_2$ embodiment, distinctive luminescence and other photochromic qualities are exhibited.

In other embodiments of the invention the metal M may be a $1^{st}$ row transition metal other than Cu or Zn, such as Sc, Ti, V, Cr, Mn, Fe, Co, or Ni, or some other transition-metal such as Zr, Nb or Ru. M may also be a lanthanide. Although the Mn $(water)^{16}$, Fe (with K-salt)$^{16}$, Co (none, with K-salt$^{17,\ 18}$, and DMF$^{19}$), Zn (none)$^{20}$ and a few lanthanides (Gd, Eu, Yb—all with no ligands)$^{21,\ 22-24}$ complexes are known in the prior art (ligands shown in brackets), no sensor or vapochromic properties for such complexes have been previously described.

Optionally, an organic ligand may be bound to M. The ligand may be any ligand capable of capping the metal cation, and may include nitrogen, oxygen, sulfur or phosphorus donors.

Depending upon the resultant charge of the $M_W[M^-_X(Z)_Y]_N$ structure, a charge-balancing ion, either a cation or anion, may also be present. For example, a charge balancing ion may be required where $M^-$ is Hg.

In alternative embodiments of the invention the metal $M^-$ may be selected to produce both linear metal cyanides or non-linear cyanides. For example, cyanometallate units such as $[Au(CN)_2]^-$, $[Ag(CN)_2]^-$ or $[Hg(CN)_2]$ may be incorporated into polymers in conjunction with different transition metal cations and supporting ligands according to the following general equation:$^{25-27,\ 28-33}$

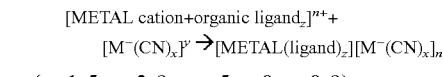

(n=1-5, x=2-9, y=−5 to 0, z=0-9)

The synthesis may be readily accomplished in solvents such as water or alcohols. Compared to prior art approaches, the polymers and polymer-analyte compositions of the present invention can be prepared from extremely simple commercially available starting materials in minimal steps. As described in the Examples section below, the synthetic methodology, which has built-in design flexibility, low-cost and simple synthesis, is also a general advantage of coordination polymer systems over current zeolitic technology. The system is modular in that the metal cation and organic ligand can be chosen as desired to target a particular application or property.

An important advantage of embodiments of the invention described herein is that the vapochromic properties of the polymers may be reversible. For example, the $Cu[Au(CN)_2]_2$ embodiment shows reversible vapochromic sensor behaviour attributable to the Cu—Au pairing.[34] Starting with a solid of any $Cu[Au(CN)_2]_2(solvent)_x$, addition of a different solvent vapour (analytes) generates a new complex. As described below, exceptions may apply in the case of very strong donor solvents such as pyridine or ammonia, which bind strongly to the $Cu^{II}$ center and are not easily displaced by other solvents. Similarly, the $Zn[Au(CN)_2]_2$ embodiment exhibits reversible vapoluminescent material qualities.[35] The polymers of the invention may thus be employed in a dynamic system for successively detecting different analytes without the need for reinitialization (although reinitialization may still be required to repeatedly detect the same analyte).

The invention may be used for detecting a wide variety of analytes including volatile organic compounds (VOCs) and gases. The solid polymers adsorb (i.e. bind or trap) analyte, such as organic solvents, exposed to the polymers in a vapour (or liquid) phase. The detectable VOCs typically include a hetero (non-carbon) atom donor such as hydrogen, nitrogen, oxygen, sulfur and phosphorus donors. Examples of solvent vapours that will effectively adsorb to the polymers of the invention include pyridine, dioxane, water, ethanethiol and trimethylphosphine. Donor gases such as $H_2S$ and ammonia also readily bind and are detectable. The binding capacity and sensitivity of the polymers may be adjusted through altering the identity of the metals M and M⁻ to enable detection of a range of gases, including but not limited to $NO_x$, $SO_x$, $CO_x$ and alkenes. For example, the zinc-based polymer described herein appears to bind $CO_2$ and may have applications as a $CO_2$-sensor.

As will be appreciated by a person skilled in the art, the polymers of the invention may find application in wide range of industrial and commercial applications, such as in the chemical, energy and environmental sectors. The polymers may be used in many different solid forms depending upon the vapochromic application, such as powders, crystals, thin films or combinations thereof. Exemplary industrial applications include: personal and badge monitors in chemical laboratories (e.g. industrial chemical or pharmaceutical research laboratories, paint and coatings manufacturing, cosmetics manufacturing) for hazardous vapour detection; portable or stationary threshold monitors for chemical vapours in laboratory environments or chemical storage facilities for hazardous vapour detection or regulated emission requirements; environmental sensor for volatile organic compounds or gases ("electronic noses") for use at environmental remediation sites, landfills, air-quality monitoring etc.; and responsive coatings, art supplies, colour-changing paint and other related applications where a colour-changing material is desired.

As will be apparent to a person skilled in the art, the vapochromic polymers described herein may be deployed in various different forms and applications for specifically detecting ammonia. For example, the polymers may be used in medical applications for sensing ammonia in the breath of patients. In one embodiment, a polymer may be embedded in a paper strip, similar to litmus paper, or onto a binding agent such as silica, which a patient would be instructed to breathe on. Many medical conditions, such as ulcers, kidney disease and liver disease, are associated with abnormally high (but still low in an absolute sense) levels of ammonia in the breath of some affected patients. Many other potential applications for detecting low levels of ammonia may also be envisioned.

Although the present invention has been principally described in relation to analyte sensing and detection, the polymers and compositions described herein may be useful for other purposes such as extraction, purification and storage applications.

EXAMPLES

The following examples will further illustrate the invention in greater detail although it will be appreciated that the invention is not limited to the specific examples.

The following description of experimental details and experimental results is presented in multiple parts. Example 1.0 describes synthetic procedures and experimental results for the $Cu[Au(CN)_2]_2(solvent)_x$ system. Example 2.0 describes a similar synthetic procedure and experimental results for an analogous $Zn[Au(CN)_2]_2(solvent)_x$ system.

Example 1.0

Cu-Based Polymers 1.1 $Cu[Au(CN)_2]_2(Solvent)_x$ System
1.1.1 Experimental Apparatus and General Procedure General Procedure and Physical Measurements. All manipulations were performed in air. All the reagents were obtained from commercial sources and used as received. Infrared spectra were recorded as KBr pressed pellets on a Thermo Nicolet Nexus 670 FT-IR spectrometer. Microanalyses (C, H, N) were performed at Simon Fraser University. Magnetic susceptibilities were measured on polycrystalline samples at 1 T between 2 and 300 K using a Quantum Design MPMS-5S SQUID magnetometer. All data were corrected for temperature independent paramagnetism (TIP), the diamagnetism of the sample holder, and the constituent atoms (by use of Pascal constants).[36] Solid-state UV-visible reflectance spectra were measured using an Ocean Optics SD2000 spectrophotometer equipped with a tungsten halogen lamp. Thermogravimetric analysis (TGA) data were collected using a Shimadzu TGA-50 instrument in an air atmosphere.

1.1.2 Synthetic Procedures

Synthesis of $Cu[Au(CN)_2]_2(DMSO)_2$, 1: A 0.5 mL dimethylsulfoxide (DMSO) solution of $Cu(ClO_4)_2.6H_2O$ (0.037 g, 0.1 mmol) was added to a 0.5 mL DMSO solution of $KAu(CN)_2$ (0.057 g, 0.2 mmol). Green crystals of $Cu[Au(CN)_2]_2(DMSO)_2$ were obtained by slow evaporation over several days, filtered and air-dried. Yield: 0.050 g, 70%. Anal. Calcd. for $C_8H_{12}N_4Au_2CuO_2S_2$: C, 13.39; H, 1.69; N, 7.81. Found: C, 13.43; H, 1.72; N, 7.61. IR (KBr): 3005 (w), 2915 (w), 2184 (s), 2151 (m), 1630 (w), 1426 (w), 1408 (w), 1321 (w), 1031 (m), 993 (s), 967 (m), 720 (w), 473 (m) cm⁻¹. The same product can be obtained by absorption of DMSO by $Cu[Au(CN)_2]_2(H_2O)_2$.

Synthesis of $Cu[Au(CN)_2]_2(DMSO)_2$, 2: A 0.2 mL DMSO solution of $Cu(ClO_4)_2.6H_2O$ (0.037 g, 0.1 mmol) was added to a 0.4 mL DMSO solution of $KAu(CN)_2$ (0.057 g, 0.2 mmol). Blue needles of $Cu[Au(CN)_2]_2(DMSO)_2$ formed after one hour and were filtered and dried under $N_2$. Yield: 0.057 g, 80%. Anal. Calcd. for $C_8H_{12}N_4Au_2CuO_2S_2$; C, 13.39; H, 1.69; N, 7.81. Found: C, 13.50; H, 1.76; N, 7.62. IR (KBr): 3010 (w), 2918 (w), 2206 (m), 2194 (s), 2176 (m), 2162 (m), 1631 (w), 1407 (w), 1316 (w), 1299 (w), 1022 (m), 991 (s), 953 (m), 716 (w), 458 (m) cm⁻¹.

Synthesis of $Cu[Au(CN)_2]_2(DMF)$, 3: A 2 mL N,N-dimethylformamide (DMF) solution of $Cu(ClO_4)_2.6H_2O$ (0.037 g, 0.1 mmol) was prepared. This solution was added to a 3 mL DMF solution of $KAu(CN)_2$ (0.057 g, 0.2 mmol). A dark blue-green mixture of powder and crystals of $Cu[Au(CN)_2]_2$(DMF) was obtained after several days of slow evaporation and was filtered and air-dried. Yield: 0.033 g, 52%. Anal. Calcd for $C_7H_7N_5Au_2CuO$: C, 13.25; H, 1.11; N, 11.04. Found: C, 13.26; H, 1.11; N, 11.30. IR (KBr): 2927 (w), 2871 (w), 2199 (s), 2171 (shoulder). 1665 (s), 1660 (s), 1492 (w), 1434(w), 1414 (w), 1384 (m), 1251 (w), 1105 (w), 674 (w), 516 (w), 408 (w) $cm^{-1}$. Single crystals of 3 were obtained by dissolving $Cu[Au(CN)_2]_2(H_2O)_2$ (5) in DMF and allowing the solution to evaporate very slowly. The single crystals and the crystal/powder mixture as prepared above had identical IR spectra. The same product can also be obtained by vapour absorption of DMF by several $Cu[Au(CN)_2]_2$ (solvent)$_x$ complexes.

Synthesis of $Cu[Au(CN)_2]_2(pyridine)_2$, 4: A 10 mL pyridine/water/methanol (5:47.5:47.5) solution of $Cu(ClO_4)_2.6H_2O$ (0.111 g, 0.3 mmol) was prepared. This solution was added to a 10 mL pyridine/water/methanol (5:47.5:47.5) solution of $KAu(CN)_2$ (0.171 g, 0.59 mmol). A blue powder of $Cu[Au(CN)_2]_2(pyridine)_2$ was obtained immediately and was filtered and air-dried. Yield: 0.163 g, 75%. Anal. Calcd for $C_{14}H_{10}N_6Au_2Cu$: C, 23.36; H, 1.40; N, 11.68. Found: C, 23.52; H, 1.44; N, 11.58. IR (KBr): 3116 (w), 3080 (w), 2179 (s), 2167 (s), 2152 (s), 2144 (m), 1607 (m), 1449 (m), 1445 (s), 1214 (m), 1160 (w), 1071 (m), 1044 (w), 1019 (m), 758 (s), 690 (s), 642 (m) $cm^{-1}$. Single crystals of 4 were obtained by slow evaporation of the remaining solution. The crystals and powder had identical IR spectra. The same product can also be obtained by vapour absorption of pyridine by several $Cu[Au(CN)_2]_2$ (solvent)$_x$ complexes.

Synthesis of $Cu[Au(CN)_2]_2(H_2O)_2$, 5: A 10 mL aqueous solution of $Cu(ClO_4)_2.6H_2O$ (0.259 g, 0.7 mmol) was prepared and added to a 10 mL aqueous solution of $KAu(CN)_2$ (0.403 g, 1.4 mmol). A pale green powder of $Cu[Au(CN)_2]_2(H_2O)_2$ formed immediately and was filtered and air-dried. Yield: 0.380 G, 91%. The same product can be obtained by vapour absorption of water by several $Cu[Au(CN)_2]_2$ (solvent)$_x$ complexes. Anal. Calcd for $C_4H_4N_4Au_2CuO_2$: C, 8.04; H, 0.67; N, 9.38. Found: C, 8.18; H, 0.71; N, 9.22. IR (KBr): 3246 (m), 2217 (s), 2194(vw), 2171 (s), 1633 (w) $cm^{-1}$.

Synthesis of $Cu[Au(CN)_2]_2$, 6: $Cu[Au(CN)_2]_2(H_2O)_2$ was heated (150° C.) in vacuo to yield green-brown $Cu[Au(CN)_2]_2$. The yield is quantitative, with no $\upsilon_{CN}$ peaks for hydrated 5 observable. Anal. Calcd for $C_4N_4Au_2Cu$: C, 8.56; H, 0; N, 9.98. Found: C, 8.68; H, trace; N, 9.80. IR (KBr): 2191 (s), 1613(vw), 530 (m) $cm^{-1}$.

Synthesis of $Cu[Au(CN)_2]_2(CH_3CN)_2$, 7: A 1 mL $CH_3CN$ solution of $Cu(ClO_4)_2.6H_2O$ (0.037 g, 0.1 mmol) was prepared and added to a 2 mL $CH_3CN$ solution of $KAu(CN)_2$ (0.057 g, 0.2 mmol). A green powder of $Cu[Au(CN)_2]_2(CH_3CN)_2$ precipitated immediately along with a white powder of $KClO_4$. To prevent the replacement of $CH_3CN$ by atmospheric water, the solvent was removed under vacuum and the $KClO_4$ side product was not removed through washing and filtering. Anal. Calcd for $Cu[Au(CN)_2]_2(CH_3CN)_2+2(KClO_4)$ ($C_8H_6N_6Au_2Cl_2CuK_2O_8$): C, 10.44; H, 0.65; N, 9.12. Found: C, 10.99; H, 0.57; N, 8.69. IR (KBr): 2297 (w), 2269 (w), 2192 (s), 1600 (w), 1445 (w), 1369 (w), 1088 (s), 941 (w), 925 (w), 752 (w), 695 (w), 626 (m), 512 (w), 468 (w), 419 (w) $cm^{-1}$. The same product (without $KClO_4$) can be obtained by vapour absorption of acetonitrile by $Cu[Au(CN)_2]_2(DMSO)_2$ (1 or 2).

Synthesis of $Cu[Au(CN)_2](dioxane)(H_2O)$, 8: A 2 mL dioxane/water (2:1) solution of $Cu(ClO_4)_2.6H_2O$ (0.037 g, 0.1 mmol) was prepared. This solution was added to a 4 mL dioxane/water (2:1) solution of $KAu(CN)_2$ (0.057 G, 0.2 mmol). A pale blue-green powder of $Cu[Au(CN)_2]_2(dioxane)(H_2O)$ was obtained immediately and was filtered and air-dried. Yield: 0.057 g, 85%. The same product can be obtained by vapour absorption of dioxane by several $Cu[Au(CN)_2]_2$ (solvent)$_x$ complexes (the water molecule included in this case is from ambient moisture). Anal. Calcd for $C_8H_{10}N_4Au_2CuO_3$: C, 14.39; H, 1.51; N, 8.39. Found: C, 14.31; H, 1.21; N, 8.43. IR (KBr): 2976 (m), 2917 (m), 2890 (w), 2862 (m), 2752 (w), 2695 (w), 2201 (s), 2172 (w), 1451 (m), 1367 (m), 1293 (w), 1255 (s), 1115 (s), 1081 (s), 1043 (m), 949 (w), 892 (m), 871 (s), 705 (w), 610 (m), 515 (m), 428 (m) $cm^{-1}$.

Synthesis of $Cu[Au(CN)_2]_2(NH_3)_4$, 9: This product was obtained by vapour absorption of NFL by several $Cu[Au(CN)_2]_2$ (solvent)$_x$ complexes. The yield is quantitative as shown by IR. Anal. Calcd for $C_4H_{12}N_8Au_2Cu$: C, 7.63; H, 1.92; N, 17.80. found: C, 7.56; H, 1.98; N, 17.71. IR (KBr): 3359 (s), 3328 (s), 3271 (s), 3212 (m), 3182 (m), 2175 (m), 2148 (s), 1639 (m), 1606 (m), 1243 (s), 685 (s), 435 (w)$cm^{-1}$.

1.1.3 X-ray Crystallographic Analysis

X-Ray Crystallographic Analysis. $Cu[Au(CN)_2]_2(DMSO)_2$ 1 and 2, $Cu[Au(CN)_2]_2(DMF)$ 3 and $Cu[Au(CN)_2]_2(pyridine)_2$ 4: Crystallographic data for all structures are collected in Table 1. Crystals 1, 3 and 4 were mounted on glass fibers using epoxy adhesive and crystal 2 was sealed in a glass capillary. Crystal 1 was a green rectangular plate ($0.09\times0.12\times0.3$ mm$^3$), crystal 2 was a pale blue needle ($0.11\times0.11\times0.2$ mm$^3$), crystal 3 was a green needle ($0.09\times0.09\times0.15$ mm$^3$) and crystal 4 was a dark blue platelet ($0.02\times0.06\times0.15$ mm$^3$).

For 1. data in the range $4°<2\theta<55°$ were recorded using the diffractometer control program DIFRAC[37] and an Enraf Nonius CAD4F diffractometer. The NRCVAX Crystal Structure System was used to perform psi-scan absorption correction (transmission range: 0.0301-0.1726) and data reduction, including Lorentz and polarization corrections.[38] All non-hydrogen atoms were refined anisotropically. Full matrix least-squares refinement (1231 reflections included) on F (93 parameters) converged to $R_1=0.042$. $wR_2=0.047$ ($I_0>2.5\sigma(I_0)$).

For 2, 3 and 4, data in the ranges $6.9°<2\theta<136.1°$, $9.2°<2\theta<144.0°$ and $12.0°<2\theta<142.6°$ respectively were recorded on a Rigaku RAXIS RAPID imaging plate area detector. A numerical absorption correction was applied (transmission range: 0.019-0.161, 0.0070-0.0199 and 0.3484-0.5826) and the data were corrected for Lorentz and polarization effects[39] For 2. the Au, Cu and S atoms were refined anisotropically, while the remainders were refined isotropically. For 3 and 4, all non-hydrogen atoms were refined anisotropically. Full matrix least-squares refinement on F was performed on 2, 3 and 4, the data converging to the following results: for 2, $R_1=0.062$, $wR_2=0.082$ ($I_0>3.0\sigma(I_0)$). 2026 reflections included, 205 parameters): for 3, $R_1=0.0315$, $wR_2=0.0456$ ($I_0>3.0\sigma(I_0)$, 1538 reflections included, 148 parameters): for 4, $R_1=0.0276$, $wR_2=0.0401$ ($I_0>3.0\sigma(I_0)$, 1021 reflections included, 107 parameters).

All structures were refined using CRYSTALS.[40] The structures were solved using Sir 92 and expanded using Fourier techniques. Hydrogen atoms were included geometrically in all structures but not refined. Diagrams were made using Ortep-3 (version 1.076)[41] and POV-Ray (version 3.6.0)[42]. Selected bond length and angles for 1-4 are reported in Tables 2 to 5 respectively.

1.1.4 Results

Synthesis. The reaction of $Cu^{II}$ salts with $KAu(CN)_2$ in dimethylsulfoxide (DMSO) produced two different compounds, depending on the total concentration of starting reagents. In dilute solution, green crystals of polymorph 1 formed slowly, whereas blue crystals of polymorph 2 were obtained rapidly in a highly concentrated solution. The IR spectra of 1 and 2 show different features (Table 6); the higher-energy bands likely correspond to bridging CN-groups, while the lower-energy bands are due to either free or loosely bound CN-groups.[43] The X-ray crystal structures of 1 and 2 revealed two different polymeric networks, both with the same empirical formula Cu[Au(CN)$_2$]$_2$(DMSO)$_2$, as confirmed by elemental analysis.

Crystal Structure of the Green Cu[Au(CN)$_2$]$_2$(DMSO)$_2$ Polymorph, 1. The five-coordinate Cu$^{II}$ center in 1 has a τ-value[44] of 0.44, where τ=0 is pure square pyramidal and τ=1 is pure trigonal bipyramidal, suggesting that the coordination geometry could be considered equally distorted from either polyhedron. The Cu$^{II}$ center is bound to two DMSO-O atoms (O—Cu—O=167.06°) and three N(cyano) atoms (FIG. 1). Selected bond lengths and angles for 1 are listed in Table 2. The asymmetric unit contains two different [Au(CN)$_2$]$^-$ units: a Cu$^{II}$-bridging moiety that generates a 1-D chain, and a Cu$^{II}$-bound dangling group. The chains stack on top of each other parallel to the (101)-plane, forming stacks of chains that are offset to allow interdigitation of the dangling [Au(CN)$_2$]$^-$ units. Each chain is connected to the four neighbouring chains through Au—Au interactions of 3.22007 (5) Å between the Au(1) atoms of each dangling group and the Au(2) atoms of the chain backbone (FIG. 2(a)). The DMSO molecules occupy the channels between the chains; these channels are delineated by both [Au(CN)$_2$] groups and Au—Au bonds (FIG. 2(b)). A viable Au—Au interaction is considered to exist when the distance between the two atoms is less than 3.6 Å. the sum of the van der Waals radii for gold.[45]

Crystal Structure of the Blue Cu[Au(CN)$_2$]$_2$(DMSO)$_2$ Polymorph, 2. The structure of poly morph 2 contains Cu$^{II}$ centers in a Jahn-Teller distorted octahedral geometry, with the two DMSO molecules bound in a cis-equatorial fashion (O—Cu—O=95.2°) rather than in the nearly 180°-arrangement in 1. Selected bond lengths and angles for 2 are found in Table 3. The four remaining sites (two axial and two equatorial) are occupied by N(cyano) atoms of bridging [Au(CN)$_2$]$^-$ units, generating corrugated 2-D sheets (FIG. 3(a)). These 2-D layers stack (FIG. 3(b)) and are held together by weak Au(1)-Au(2) interactions of 3.419 (3) Å and perhaps weak Au(3) . . . Au(4) contacts of 3.592(4) Å. Thus, the colour difference between the two polymorphs can be attributed to the different coordination number and geometry around the Cu$^{II}$ centers. That said, the coarse features of 1, namely the rectangular "channels" filled with DMSO molecules, are also clearly delineated in 2.

Magnetic Properties. As polymorphs 1 and 2 clearly have significantly different solid-state structures, it follows that their physical and chemical properties may also vary: this is obviously the case for their solid-state optical reflectance spectra, which show $\lambda_{max}$ of 550±7 and 535±15 nm respectively (Table 6). To explore this key issue, a series of representative properties were investigated. For example, the magnetic susceptibilities of 1 and 2 were measured at temperatures varying from 300 to 2 K. At 300 K, $\mu_{eff}$=1.98 and 1.93 $\mu_B$ for 1 and 2 respectively, typical for Cu$^{II}$ centers.[46] As the temperature drops, $\mu_{eff}$ decreases and reaches 1.74 and 1.67 $\mu_B$ at 2 K for 1 and 2 respectively. There is no maximum in either $\chi_M$ vs T plot. This behaviour is consistent with weak antiferromagnetic coupling, probably mediated by the diamagnetic Au$^I$ center.[25-27, 47] Thus, the two polymorphs have similar magnetic properties.

Thermal stability. Examining the thermal stabilities of 1 and 2 by thermogravimetric analysis (FIG. 4). 1 loses its first DMSO molecule from 150-190° C., and the other one from 210-250° C. For polymorph 2 (which has 4 crystallographically distinct DMSO molecules), the first two DMSO molecules are lost between 100-135° C., and then 150-190° C. while the two remaining DMSO molecules dissociate around 210-250° C. comparable with 1. Both polymorphs are then stable until ~310° C., at which point cyanogen (C$_2$N$_2$) is released, consistent with the decomposition of the Cu[Au(CN)$_2$]$_2$ framework.[48] Hence, the thermal stabilities of the two polymorphs with respect to the loss of the first DMSO molecules are significantly different. Differential scanning calorimetry shows no evidence for the thermal interconversion in the solid state from 2 to 1 below the decomposition temperature of 2.

Vapochromic Behavior. Interestingly, even though both polymorphs are thermally stable up to at least 100° C. the DMSO molecules can easily be replaced by ambient water vapour at room temperature to yield Cu[Au(CN)$_2$]$_2$(H$_2$O)$_2$ (5), as shown by elemental and thermogravimetric analysis. Despite the fact that both polymorphs have different solid-state structures. IR spectroscopy and powder X-ray diffraction show that both polymorphs convert to the same Cu[Au(CN)$_2$]$_2$(H$_2$O)$_2$ (5) complex (Table 6). This conversion is reversible. However, if DMSO vapour is added back to 5, only the green polymorph Cu[Au(CN)$_2$]$_2$(DMSO)$_2$(1) is formed, even if the original DMSO-complex to which H$_2$O was added was the blue polymorph (2). The exchange of DMSO for H$_2$O can be observed visually from the associated colour change (FIG. 5).

Cu[Au(CN)$_2$]$_2$(DMSO)$_2$ (either 1 or 2) also displays vapochromic behaviour when exposed to a variety of other donor solvent vapours (i.e. analytes) in addition to H$_2$O. Each Cu[Au(CN)$_2$]$_2$ (solvent)$_x$ complex can be distinguished easily by its colour (FIG. 5 and Table 6). In addition, the $\upsilon_{CN}$ region of the IR spectrum for each solvent complex is a characteristic, sensitive signature for that solvent (Table 6). FIG. 10 is a spectrograph showing the comparative IR spectra in the cyanide region for three solvents (i.e. analytes), namely pyridine, DMF and water using the Cu[Au(CN)$_2$]$_2$ (solvent)$_x$ polymer. FIG. 10 show graphically the characteristic, sensitive signature for each solvent in the $\upsilon_{CN}$ region of the IR spectrum. Thus both the visible colour changes and the cyanide-IR changes are dramatic and distinctive for each analyte, allowing for more specific and sensitive analyte detection.

Importantly, this solvent exchange is completely reversible, thus permitting dynamic solvent sensing. As indicated in the above synthetic examples, starting with a solid of Cu[Au(CN)$_2$]$_2$ (solvent)$_x$, addition of a different solvent vapour generates a new complex. The only exceptions occur in the case of very strong donor solvents such as pyridine or ammonia, which bind strongly to the Cu$^{II}$ center and are not easily displaced by other solvents.

Each Cu[Au(CN)$_2$]$_2$ (solvent)$_x$ complex was also synthesized by reacting Cu(II) salts with [Au(CN)$_2$]$^-$ in the appropriate solvent and each was found, by elemental analysis, IR spectroscopy, TGA, and crystallography, to be identical to the complex generated by solvent exchange. In every case, elemental analysis and TGA (Table 7) indicate that the number of solvent molecules incorporated into the complex per transition metal center is always the same as the number incorporated by vapour adsorption. This is easily rationalized by the fact that all adsorbed solvent molecules are ligated to the Cu$^{II}$ center in a 1:1.1:2 or, in the case of ammonia, a 1:4 ratio, with no additional loosely trapped solvent molecules in channels (as shown by TGA. Table 7), as is often observed in other porous systems that include solvent.[49-52]

Crystal Structure of Cu[Au(CN)$_2$]$_2$(DMF), 3. In order to better understand the structural changes that occur during a vapochromic response of the DMSO polymorphs, the structures of Cu[Au(CN)$_2$]$_2$(DMF) (3) and Cu[Au(CN)$_2$]$_2$(pyridine)$_2$ (4) were investigated. The structure of 3 contains Cu$^{II}$ centers with a square-pyramidal geometry, where the four basal sites are occupied by N(cyano) atoms of bridging [Au(CN)$_2$]$^-$ units and the apical site is occupied by an O-bound DMF molecule. Selected bond lengths and angles for 3 are listed in Table 4. The alternation of Cu$^{II}$ centers and [Au(CN)$_2$]$^-$ units generates a 2-D square grid motif with all the DMF molecules pointing either above or below the plane of the sheet (FIG. 6(a)). This grid is similar to that observed in the blue Cu[Au(CN)$_2$]$_2$(DMSO)$_2$ complex (2) if one DMSO molecule was removed and the corrugation reduced. The layers stack on top of each other in an offset fashion, thereby disrupting any channels, and are held together by Au(1)-Au(1*$^a$) and Au(2)-Au(2*$^b$) interactions of 3.3050 (12) Å and 3.1335 (13) Å (FIG. 6(b)).

Crystal Structure of Cu[Au(CN)$_2$]$_2$(pyridine)$_2$, 4. The structure of 4 is similar to that of 3, except that the Cu$^{II}$ centers are surrounded by two solvent molecules, generating octahedrally coordinated metals. The axial sites and two of the equatorial sites are occupied by N(cyano) atoms of bridging [Au(CN)$_2$]$^-$ units. Pyridine molecules occupy the two other equatorial sites. Selected bond lengths and angles for 4 are listed in Table 5. As observed for 3, infinite 2-D layers are obtained (FIGS. 7(a) and (b)). No aurophilic interactions are present between the Au atoms of neighboring sheets, but π-π interactions of ~3.4 Å are found between stacked pyridine rings of adjoining sheets. Thus, the square-grid array present in 2 and 3 is maintained but in this case the sheets are completely flat, as opposed to the corrugated array found in 2. The 180° disposition of the pyridine rings (vs. the cis orientation of the DMSO molecules in 2) also serves to separate the sheets, disrupting potential intersheet Au—Au interactions.

Solvent free Cu[Au(CN)$_2$]$_2$, 6. The green-brown solvent-free complex. Cu[Au(CN)$_2$]$_2$ (6), was also prepared by thermally removing in vacuo the water molecules from 5. Changes in the powder X-ray diffractogram and in the $\upsilon_{CN}$ peaks of 6 indicate that some rearrangement in the framework occurred. The IR spectrum only shows one stretching frequency (2191 cm$^{-1}$), indicating that all CN groups are in a similar environment, reminiscent of the Cu[Au(CN)$_2$]$_2$(DMF) structure. This is also comparable with the results published for the Mn[Au(CN)$_2$]$_2$(H$_2$O)$_2$[16] and the Co[Au(CN)$_2$]$_2$(DMF)$_2$[19] systems (which show stretches at 2150 and 2179 cm$^{-1}$ respectively). In these two coordination polymers, the M[Au(CN)$_2$]$_2$ unit (M=Mn or Co) forms 2-D square grids, with solvent molecules hanging above and below the plane of the sheet. Although the three-dimensional topology of Cu[Au(CN)$_2$]$_2$ is not known, it likely forms a similar 2-D square grid network with all N(cyano) atoms equatorially bound to a square planar Cu$^{II}$ center (FIG. 8), as would be generated by structurally erasing the DMF molecule from 3. The Cu[Au(CN)$_2$]$_2$ system was found to be only slightly porous by N$_2$-adsorption measurements, suggesting that the 2-D sheets stack in an offset fashion, likely with significant aurophilic interactions, thereby blocking channel formation. Despite this, solvents are still taken up by this system to yield the same Cu[Au(CN)$_2$]$_2$ (solvent)$_x$ complexes.

Concentration-controlled synthesis of structural isomers of coordination polymers Results obtained by X-ray crystallography and elemental analysis indicate that 1 and 2 of this Example are true polymorphs or supramolecular isomers, as opposed to pseudopolymorphs that differ by incorporation of varying amounts or identities of co-crystallized solvent molecules.[53, 54] As mentioned above, many factors contribute to the preferential formation of one polymorph over another and it can often be a challenge to control the synthesis of a desired isomer.[53-57] Varying crystallization conditions, such as solvent type, starting materials, temperature and concentration are often important to ensure generation of just one polymorph. For example, crystallizing Ni[Au(CN)$_2$]$_2$(en)$_2$ (en=1,2-ethylenediamine) from [Ni(en)$_3$]Cl$_2$.2H$_2$O or [Ni(en)$_2$Cl$_2$] generates molecular and 1-dimensional polymorphic materials respectively.[47] Also, it has been shown that metastable polymorphs can be obtained by rapid crystallization from a supersaturated solution, e.g., via a fast drop in temperature.[56, 58] For example, {Cu[N(CN)$_2$]$_2$(pyrazine)}$_n$ forms green/blue and blue polymorphs when crystallized from concentrated and dilute solution respectively.[59]

Similarly, in the Cu[Au(CN)$_2$]$_2$(DMSO)$_2$ system described in this Example, if the total concentration of reagents is below 0.2 M, 1 is formed, while 2 is obtained exclusively from >0.5 M solutions. The concentration-controlled synthesis of structural isomers of coordination polymers is uncommon relative to examples with molecular systems.[59, 60] This concentration dependence suggests that green 1 is the thermodynamic product, while blue 2, which rapidly precipitates from solution, is likely a kinetic product. The fact that Cu[Au(CN)$_2$]$_2$(H$_2$O)$_2$ converts exclusively to the green polymorph 1 when adsorbing DMSO is further evidence that 1 is the most energetically favorable polymorph. Interestingly, the density of thermodynamically preferred 1 is actually lower than that of 2. This surprising situation has been observed in other polymorphs.[61] Although it is unclear if this result can be attributed to entropic or enthalpic contributions, it is conceivable that the formation of shorter Au—Au bonds in 1 relative to 2 could be an important energetic factor.

Metal-ligand superstructures It has been recognized that a system does not need to be porous in order to undergo guest uptake.[62] For example, a flexible metal-ligand superstructure can dynamically adapt in order to accommodate a variety of potential guests.[62-68] In this light, the Jahn-Teller influenced flexible coordination sphere and the greater lability of Cu$^{II}$ compared with other transition metals are likely important features of the Cu[Au(CN)$_2$]$_2$ (solvent)$_x$ system. The related Mn[Au(CN)$_2$]$_2$(H$_2$O)$_2$ and Co[Au(CN)$_2$]$_2$(DMF)$_2$ systems previously reported form more rigid frameworks.[16, 19] For these two systems, thermal treatment is required to remove the guest molecules and yield compounds exhibiting zeolitic properties. The lability of Cu$^{II}$ in the system of the present invention facilitates the reversible exchange of adsorbed solvent molecules without any thermal treatment required. It also likely increases the flexibility of the framework by allowing the breaking and the reformation of Cu—N(cyano) bonds, thereby adapting to the solvent guest present. Gold-gold interactions are probably present in all the Cu[Au(CN)$_2$]$_2$ (solvent)$_x$ complexes and help to stabilize the 3D-network as solvent exchange takes place.

Taking into account the varied structures of the Cu[Au(CN)$_2$]$_2$ (solvent)$_x$ complexes, several modes of flexibility within the fundamental structural framework, i.e. the two-dimensional square-grid network of the Cu[Au(CN)$_2$]$_2$ moiety (FIG. 8), can be identified. Firstly, the 2-D square-grid can lie entirely flat, as in the bis-pyridine or mono-DMF complexes 3 and 4, or it can buckle to generate a corrugated 2-D array, as observed in the blue bis-DMSO polymorph 2. The extent of this corrugation can even force the partial fragmentation of the square array via the breaking of one Cu—N(cyano) bond, as observed in the green bis-DMSO polymorph 1. Such fragmentation is probably also present in the Cu[Au(CN)$_2$]$_2$(NH$_3$)$_4$ complex (9); the Cu$^{II}$ center in 9 is likely still octahedral, with two Cu—N(cyano) bonds (out of four in the fundamental square-grid structure) breaking completely to make way for two additional NH$_3$ ligands, thereby disrupting the 2-D array. Another mode of flexibility lies in the ability of the Cu$^{II}$ center to readily alternate between being five- and six-coordinate, as well as accessing a range of five-coordinate geometries. This adaptability is independent of the extent of corrugation: five-coordinate Cu$^{II}$ centers are found in both flat 3 and corrugated 1 while six-coordinate centers are present in both flat 4 and corrugated 2. Finally, the Jahn-Teller distortions endemic to Cu$^{II}$ complexes yield a third mode of flexibility: the arrangement of equatorial/axial or basal/apical N(cyano) ligands and donor solvents. Again, this pliability is independent of the extent of corrugation: both the five-coordinate DMF complex 3 and six-coordinate bis-pyridine complex 4 contain flat Cu[Au(CN)$_2$]$_2$ square-grids, but in 3 the N(cyano) ligands are all basal (and therefore roughly identical in length) while in 4 two N(cyano) ligands are equatorial and two are axial, leading to significantly different Cu—N (cyano) bond lengths. This form of structural flexibility is particularly important since substantially different IR signatures in the cyanide region are generated depending on the N(cyano) bonding arrangement in the system. Of course, all three modes of flexibility work in concert to generate the adaptable, dynamic network solid that is ultimately able to bind and sense different donor solvents.

The source of the vapochromism in the Cu[Au(CN)$_2$]$_2$ (solvent)$_x$ system differs from that of other Au$^I$-containing systems.[3-6] Cu[Au(CN)$_2$]$_2$ (solvent)$_x$ shows vapochromism in the visible since each donor solvent molecule that is adsorbed binds to the Cu$^{II}$ center and modifies differently the crystal field splitting. As a consequence, the colour of the vapochromic compound changes as the d-d absorption bands shift with donor. In addition to donor identity, the resulting coordination number (five or six) and specific geometry of the copper center also influences the colour of the complexes by altering the splitting of the d-orbitals.

The [Au(CN)$_2$]$^-$ unit is also a key component of this system since it telegraphs the changes in solvent bound to the Cu$^{II}$ centers via the $\upsilon_{CN}$ stretch. Each Cu[Au(CN)$_2$]$_2$ (solvent)$_x$ has a different IR signature since every VOC modifies in a different manner the electron density distribution around the Cu$^{II}$ center. This influences the amount of π-back bonding from the Cu$^{II}$ center to the CN group, which in turn is observed in the IR spectrum due to the change in vibration frequency.[43] Also, the number of bands observed is related to the symmetry and coordination number of the Cu$^{II}$ centers, as described in detail above.

In summary, it has been illustrated in this Example that, despite their different solid-state structures, the two Cu[Au(CN)$_2$]$_2$(DMSO)$_2$ polymorphs exhibit the same vapochromic behaviour with respect to sorption of analytes such as VOCs. The use of [Au(CN)$_2$]$^-$ as a building block is important to the function of this vapochromic coordination polymer. First, it provides the very sensitive CN reporter group that can allow IR-identification of the solvent adsorbed in the materials. Also, Au—Au interactions via the [Au(CN)$_2$]$^-$ units increase the structural dimensionality of the system in most cases and probably help provide stabilization points for the flexible Cu[Au(CN)$_2$]$_2$ framework.

1.2 Cu[Au(CN)$_2$]—Based Sensing of Ammonia and Amines

In this example coordination polymer Cu[Au(CN)$_2$]$_2$(µ-H$_2$O)$_2$ (5) was shown to be effective in reversibly sensing ammonia and amines at low concentrations.

As indicated above, Cu[Au(CN)$_2$]$_2$(µ-H$_2$O)$_2$ 5 is a green powder which, upon exposure to vapours of volatile organic compounds, exhibits visible vapochromism and changes in the $\upsilon_{CN}$ region of the IR spectrum. In this example, a finely ground powder of Cu[Au(CN)$_2$]$_2$(µ-H$_2$O)$_2$ (5) deposited onto a CaF$_2$ plate was exposed to a series of solvent vapours in a range of concentrations in order to determine sensitivity levels. Use of the $\upsilon_{CN}$ IR signature was more sensitive than use of the colour change monitored by UV-Vis solid state reflectance for all analytes: sensitivity limits for a range of VOCs via both detection channels are reported in Table 8.

Consistent with the vapochromic mechanism, which requires that the analyte ligate to the copper(II) center, 5 was found to be insensitive to non-coordinating or very weakly coordinating classes of VOCs (with respect to copper(II)) and related analytes. A representative set of compounds (in brackets) covering a range of functional groups such as esters (ethyl acetate), ethers (tetrahydrofuran), ketones (acetone), thiols (tetrahydrothiophene), aldehydes (formaldehyde), saturated hydrocarbons (pentane), aromatic hydrocarbons (benzene), chloroalkanes (dichloromethane) and even, remarkably, concentrated acetic acid, all generated no response from 5, which remained unscathed after exposure to saturated atmospheres of the respective VOCs. Compound 5 generated vapochromic responses to weak donors such as DMSO, DMF and MeCN (Table 8), with IR-sensitivities in the range of 400-1000 ppm, while stronger nitrogen-based donor VOCs and ammonia had much higher sensitivities, from several-hundred ppm down to ppb levels.

Among a series of representative amines, 5 was found to be more sensitive to primary (1°) amines versus secondary and tertiary (2° and 3°) amines. This observation is likely attributable to the higher steric hindrance of 2° and 3° amines (or long-chain 1° amines such as butylamine) restricting their donor ability, rather than their increasing vapour pressures: the boiling point of pyridine (115° C.) and ethylenediamine (118° C.) are similar, yet their sensitivities are 400 ppm vs. 385 ppb respectively. Similarly, although the boiling point of ethylenediamine (118° C.) is significantly higher than diethylamine (55° C.), 5 was much more sensitive towards ethylenediamine. In the case of propylamine and butylamine, since their basicity and boiling points are fairly similar, the large decrease in sensitivity (140 ppb vs. 100 ppm respectively) probably reflects the limited ability of the flexible coordination polymer structure to readily adapt to accommodate longer chain alkyl groups.

Indeed, as shown in Table 8 below, 5 was found to be extremely sensitive to ammonia and low molecular-weight 1°-amines. For example, the detection limit with the naked eye (by watching the colour change) when 5 is exposed to ammonia is as low as 40 ppm; with visible reflectance spectroscopy and using the spectrum of 1 as a background, it drops to 230 ppb. By using the $\upsilon_{CN}$ IR spectroscopy channel, ammonia concentrations as low as 36 ppb could be detected. Similarly, propylamine could be detected down to 140 ppb.

Titration studies. Titration of 5 with consecutive equivalents of ammonia or propylamine showed that a series of intermediates were obtained en route to the final products observed upon exposure to a large excess. Monitored by IR spectroscopy, 5 interacts with ammonia and amines in a similar manner. Titration with two or less equivalents of NH$_3$ per Cu(II) centre of 5 causes a decrease in the $\upsilon_{CN}$ bands attributable to 5 at 2216 and 2171 cm$^{-1}$ and the formation of two new bands at 2181 and 2151 cm$^{-1}$. Upon continuing the titration from two to four equivalents of ammonia, new $\upsilon_{CN}$ peaks at 2175 and 2148 cm$^{-1}$ replaced the 2181/2151 cm$^{-1}$ set. Finally, further titration (up to 35 equiv.) generated the final NH$_3$-saturated film that exhibited a new $\upsilon_{CN}$ band at 2141 with a small band at 2136 cm$^{-1}$. This titration data suggests that two intermediates of stoichiometry Cu[Au(CN)$_2$]$_2$(NH$_3$)$_2$ (9) and Cu[Au(CN)$_2$]$_2$(NH$_3$)$_4$ (10) are formed on the way towards the final saturated product. Note that the IR spectrum of 9 matches that observed for the low-concentration/high sensitivity tests of 5 with NH$_3$ (Table 8).

The presence of two $\upsilon_{CN}$ bands for all intermediates and the product also indicates that two different cyanide environments exist in the solids.

A similar trend was observed for the propylamine titration of 5: one equivalent of propylamine vapour generated new peaks at 2185 and 2155 cm$^{-1}$, along with the peaks of 5 at 2216 and 2171 cm$^{-1}$. Addition of a second equivalent of propylamine greatly increased the peaks at 2185 and 2155 cm$^{-1}$ with a concomitant loss of the peaks for 5. A third equivalent of propylamine generated three new peaks at 2182, 2142 and 2133 cm$^{-1}$ with a decrease in the intensity of the 2185/2155 cm$^{-1}$ set: these peaks became dominant upon addition of a fourth equivalent. Excess propylamine generates a peak at 2143 cm$^{-1}$. The propylamine titration results also suggest the presence of two intermediates, namely Cu[Au(CN)$_2$]$_2$(CH$_3$CH$_2$CH$_2$NH$_2$)$_2$ (11) and Cu[Au(CN)$_2$]$_2$(CH$_3$CH$_2$CH$_2$NH$_2$)$_3$ (12) prior to saturation.

These titrations were also monitored by visible reflectance spectroscopy due to the drastic colour changes from green to blue-green to deep blue that occur upon exposure of 5 to ammonia or propylamine. When 5 is exposed to one to two equivalents of ammonia the $\lambda_{max}$ shifts from 535 to 510 nm with one isosbestic point at 522 nm suggesting that there are two compounds in equilibrium, most probably the starting material and the Cu[Au(CN)$_2$]$_2$[NH$_3$]$_2$ complex. When exposed to three to six equivalents of ammonia, the $\lambda_{max}$ shifts up to 470-485 nm with another crude isosbestic point at approximately 500 nm suggesting that another set of two compounds are in equilibrium, most probably the bis- and the tetrakis-ammine coordinated complexes 9 and 10. It was observed that the maxima obtained after exposing 5 to 1 and 2 equivalents of ammonia and allowing it to equilibrate are very close and the same trend is observed when exposing it to 3 to 4 equivalents of ammonia, suggesting that there are two intermediates formed Cu[Au(CN)$_2$]$_2$[NH$_3$]$_x$ (x=2.4) before it sees an excess of ammonia, which generates a maximum at 435 nm.

When 5 was titrated with propylamine vapour, the same blue-shifting trend was observed as for the ammonia analyte. Thus, the addition of one and two equivalents of propylamine shifted the visible reflectance spectrum from 535 to 502 nm, with a clear isosbestic point at 513 nm. Titration with a third equivalent of propylamine caused a further shift to 462 nm, with a new isosbestic point at 491 nm; a fourth equivalent initiated no further shift in this case. The presence of two separate isosbestic points and the titration equivalents needed to maximize the bands (two and three equiv.) are consistent with the proposed formation of intermediates 11 and 12. Addition of an excess of propylamine (14 equivalents) shifted $\lambda_{max}$ to 428 nm, generating a dark blue compound. When saturated with ammonia or propylamine, the observed UV-Vis maxima are unique to each analyte, since the ammonia/propylamine binds to the copper(II) centre and each has a different ligand field strength: the same can be said for the other strongly-bonding analytes in Table 8.

Kinetics of vapochromic response. Kinetic studies of analyte adsorption/desorption were also performed on the coordination polymer 5 by exposing it to an excess of ammonia and propylamine vapour over a period of 2 minutes. When exposed to ammonia, one isosbestic point was observed at 2175, suggesting that two compounds were in equilibrium. The $\upsilon_{CN}$ stretches were recorded with respect to time after the exposure of compound 5 to ammonia and it was observed that the band of the dry coating at 2171 and 2216 cm$^{-1}$ shifts to 2181 and 2151 cm$^{-1}$ first, which matches the value obtained for Cu[Au(CN)$_2$]$_2$[NH$_3$]$_2$ using both IR titration studies and synthetic studies. With time peaks at 2175 and 2148 cm$^{-1}$ are formed, which matches the value obtained for Cu[Au(CN)$_2$]$_2$[NH$_3$]$_4$ as described above. After some time, compound 5 sees an excess ammonia and hence a peak at 2141 cm$^{-1}$ was observed due to the presence of free Au(CN)$_2^-$.

A stepwise blue-shifting of the visible absorption band is observed over the same time-period for ammonia adsorption. However, the presence of dynamic mixtures of adducts renders the shifting conglomerate bands difficult to assign based on their maxima; however, the end-point is the fully saturated system at 435 nm.

Desorption of NH$_3$ analyte from the copper center is also observed when the cell is opened to air at room temperature. Kinetic studies were also performed on the desorption of ammonia over two minutes from a mixture of 10 and the fully saturated species at 2175/2148 and 2141/2136 cm$^{-1}$ respectively; the bis-ammonia adduct 9 rapidly grew in at 2181/2150 cm$^{-1}$, confirming the loss of two ammonia molecules. A visible colour change is also observed from blue to green with the final visible maximum at 525 nm (a mixture of 5 and 9) over 2 minutes. Note that the desorption of ammonia is very quick and hence as soon as the cell is opened loss of ammonia commences.

Analogous kinetic studies with propylamine as analyte also showed the formation of intermediates. When compound 5 was exposed to a small excess of propylamine, a shift in the IR $\upsilon_{CN}$ stretches of the starting material with respect to time was observed. The $\upsilon_{CN}$ stretches shifts from 2171 and 2216 cm$^{-1}$ to 2155 and 2187 cm$^{-1}$, consistent with the formation of Cu[Au(CN)$_2$]$_2$[CH$_3$CH$_2$CH$_2$NH$_2$]$_2$ (11). With time the peak at 2155 cm$^{-1}$ decreases and the peaks at 2182, 2140 and 2133 cm$^{-1}$ increase, analogous to Cu[Au(CN)$_2$]$_2$[CH$_3$CH$_2$CH$_2$NH$_3$]$_3$ (12).

Desorption of propylamine from the copper centre was also observed when the cell containing compound 5 and propylamine vapour was opened to air at room temperature. The IR $\upsilon_{CN}$ stretches for Cu[Au(CN)$_2$]$_2$[CH$_3$CH$_2$CH$_2$NH$_3$]$_3$ 12 moved from 2182, 2140 and 2133 cm$^{-1}$ to 2155 and 2187 cm$^{-1}$, analogous to Cu[Au(CN)$_2$]$_2$[CH$_3$CH$_2$CH$_2$NH$_2$]$_2$11, as analysed by IR titration and synthetic studies. A peak at 2171 cm$^{-1}$ attributable to the hydrate 5 also grew in over time; exposing the sample to a high humidity (68%) atmosphere for two hours, sharp peaks at 2171 and 2216 cm$^{-1}$ were observed with residual peaks at 2155 and 2187 cm$^{-1}$ corresponding to Cu[Au(CN)$_2$]$_2$[CH$_3$CH$_2$CH$_2$NH$_2$]$_2$ 11. However, at low humidity, the Cu[Au(CN)$_2$]$_2$[CH$_3$CH$_2$CH$_2$NH$_2$]$_2$ 11 compound is not reversible unless a burst of heat is applied (to give the anhydrous complex. Cu[Au(CN)$_2$]$_2$).

Upon absorption of propylamine by 5, blue shifts occur but, as with the NH$_3$ case, the presence of a dynamic mixture of Cu[Au(CN)$_2$]$_2$[CH$_3$CH$_2$CH$_2$NH$_2$]$_x$ compounds, each with a different absorption band, precluded a detailed analysis of the changes; the final visible maximum (broad. 425-440 nm) after saturation corresponds to a mixture of 11 and the saturated species 12. Upon desorption, the band red-shifts and broadens but, as is evident from the IR-data, does not rapidly settle to a single compound—it represents a mixture of bis-propylamine 11 and hydrate 5.

In general, the response time of 5 depends greatly on the analyte (Table 8) and is longer with vapour-saturated dimethylformamide, Dimethylsulfoxide, pyridine and acetonitrile (minutes to hours) vs, ammonia (<5 seconds). At lower vapour concentrations of analyte, the response times increase, to within a minute for NH$_3$, for example.

Resetting the vapochromic material. Upon standing in an NH$_3$-free environment at high humidity, 5 loses all bound ammonia and propylamine within 2 hours as determined by IR and UV-Vis spectroscopy. However, in order to quickly and fully liberate bound analyte and thereby fully reset the sensor, 5 was heated at 160° C. for 150 seconds. Rather than regenerate 5 exactly, the related anhydrous $Cu[Au(CN)_2]_2$ complex 6 was produced, as confirmed by the single $\upsilon_{CN}$ stretch at 2191 $cm^{-1}$. This material reacts in the same fashion with $NH_3$ as 5 to reform 9 but the sensitivity is three times lower than the original hydrated 5 and its response time is also slower. Thus, in the absence of high humidity or a heating reset, 5 acts primarily as a sensitive one-time dosimeter for ammonia and 1°-amines. Using a heating reset, the sensor was repeatedly cycled a further three times with no apparent degradation or change in performance.

On the other hand, when exposed to more weakly-bound analytes such as DMF, DMSO, pyridine and acetonitrile, the material will reset to the analyte-free hydrated 5 at room temperature in ambient atmosphere upon removal of the analyte vapour; the speed of this regeneration depends on the specific analyte and ambient humidity but range from seconds for acetonitrile to minutes for pyridine. Thus, for these analytes, 5 acts as a reversible sensor; repeating the cycle several times caused no apparent degradation of the material.

The potential cross-interference of different VOCs with ammonia was also analyzed by introducing mixtures of $NH_3$ and another VOC to 5; only small alkyl chain 1°-amines interfere with the $NH_3$ sensory response and even then only if they are present at a higher concentration than the ammonia. Other coordinating VOCs such as pyridine, acetonitrile, DMF and DMSO do not interfere. A high level of humidity has an impact on the vapochromic response of 5 to weaker donating solvents (DMSO, DMF, pyridine, acetonitrile etc.) but not with $NH_3$ or small 1° amines.

As will be apparent to a person skilled in the art, the quantitative values referred to in this example are guidelines only and are subject to a margin of error. The detection sensitivity of a particular vapochromic polymer to a particular analyte will vary depending upon various factors including atmospheric conditions, the manner in which the polymer is deployed and the concentration of the polymer.

Example 2.0

Zn-Based Polymers 2.1 $Zn[Au(CN_2]_2Solvent)_x$ System

Synthesis of $Zn[Au(CN)_2]_2(DMSO)_2$. To a 1 mL DMSO solution of $Zn(ClO_4)_2(H_2O)_6$ (0.032 g, 0.086 mmol) was added $KAu(CN)_2$ (0.050 g, 0.173). Slow evaporation yielded crystals of $Zn[Au(CN)_2]_2(DMSO)_2$. Anal. Calcd. for $C_8H_{12}N_4Au_2O_2S_2Zn$: C, 13.35; H, 1.68; N, 7.79%. Found: C, 13.50; H, 1.72; N, 8.04%. IR (KBr. $cm^{-1}$) 3009 (m), 2919 (m), 2849 (w), 2186 (s), 2175 (s), 1409 (m), 1314 (m), 1299 (m), 1031 (m), 1013 (s), 1005 (s), 957 (m), 710 (w).

Although the structure of a solvent-free $Zn[Au(CN)_2]_2$ polymer (13) is known, it is believed that no luminescence or analyte binding properties have previously been reported. FIG. 9 consists of photographs showing changes in luminescence in a $Zn[Au(CN)_2]_2(analyte)_x$ system under room light (top) and ultraviolet light (bottom). From left to right in the dish, the analyte is None. $NH_3$, pyridine, $CO_2$ and DMSO. As in Example 1.0 above, the cyanide-IR changes are also dramatic and distinctive for each analyte.

The zinc-based polymer described herein appears to bind $CO_2$ Anal. Calcd. for $C_5N_4Au_2O_2Zn$: C, 9.89; H, 0.00; N, 9.22%. Found: C, 9.73; H, 0.00; N, 9.32%. IR (KBr. $cm^{-1}$): 2192 (s), 2.2 Synthesis, Structure And Photoluminescent Properties of Four Polymorphs of $Zn[Au(CN)_2]_2$ (13)
2.2.1 General Procedures and Physical Measurements All manipulations were performed in air. [$^nBu_4N$][Au (CN)$_2$] ½ $H_2O$ was synthesized as previously described.[69] All other reagents were obtained from commercial sources and used as received. Infrared spectra were recorded as pressed KBr pellets on a Thermo Nicolet Nexus 670 FT-IR spectrometer. Microanalyses (C, H, N) were performed at Simon Fraser University on a Carlo Erba EA 1110 CHN Elemental Analyzer. Thermogravimetric analysis (TGA) data were collected using a Shimadzu TGA-50 instrument heating at 1° C./min in an air atmosphere. Differential Scanning Calorimetry (DSC) measurements were collected on a Perkin Elmer DSC 7 instrument with a Perkin Elmer TAC 7/DX controller heating at 2° C./min from 25-300° C.

Solid-state luminescence data were collected at room temperature on a Photon Technology International (PTI) fluorometer, using a Xe arc lamp and a photomultiplier detector. Finely ground powder samples were drop cast, from the synthesis solvent, on a quartz plate and placed at an approximately 45° angle in a quartz cuvette. Ammonia exposure experiments were conducted under the same conditions, sealing the top of the cuvette with parafilm to prevent rapid loss of ammonia gas. The headspace of a bottle of concentrated ammonia solution (29.4%) was used as the source of ammonia gas.

Emission lifetimes data were determined using a customized apparatus (Prof. K. Sakai, Kyushu University) equipped with an Iwatsu DS-4262 Digital Oscilloscope and a Hamamatsu R928/C3830 photomultiplier tube coupled to a Horiba H-20-VIS grating monochromator. The excitation source was an N2 laser (337 nm) (Usho KEN-1520).

Nitrogen porosity measurements at 77 K of 13α-13δ were carried out on a custom-built vacuum line (Prof. I. Gay, Simon Fraser University) using a gas-volumetric measurement technique. Samples of α-δ were pretreated by heating to 150° C. under vacuum in order to degas the sample and remove any surface-bound solvent. A maximum pressure of 80 Torr was used.

The vapochromic behaviour of the polymorphs 13α-13δ was quantified in a customized chamber of known volume. The visible emission spectrum was monitored using an Ocean Optics QE65000 spectrometer with an Ocean Optics deuterium/tungsten-halogen DH-2000-FHS source. Titration and sensitivity limit studies were both performed on the different polymorphs, by introducing a known amount of $NH_3$ (as 2.0 M $NH_3$ solution in 2-propanol) into the chamber through a septum using an air-tight syringe.

The sensitivity of the different polymorphs to $NH_3$ was determined by sequentially introducing known concentrations of $NH_3$ into the chamber and observing any change in visible emission at 520 nm. The 520 nm wavelength was chosen to ensure that no peak overlap was observed. The emission spectrum of the appropriate $NH_3$-free polymorph starting material was used as the background; this yielded higher sensitivities than use of a MgO white background.

The titration studies were performed by adding sequential equivalents of $NH_3$ per $Zn(II)$ centre, allowing the material in the chamber to equilibrate for 30 seconds, and then measuring the IR spectrum.

2.2.2 Synthetic Procedures

Although the inventors have experienced no difficulties, perchlorate salts are potentially explosive and should only be used in small quantities and handled with care.

α-$Zn[Au(CN)_2]_2$ (13α). A 15 mL aqueous solution containing $Zn(ClO_4)_2$ 6$H_2O$ (37 mg, 0.10 mmol) was added to a 15 mL aqueous solution of KAu(CN)$_2$ (57 mg, 0.20 mmol). Crystals begin to form after two days of slow, partial, evaporation yielding colourless X-ray quality crystals of α-Zn[Au(CN)$_2$]$_2$. (α). Yield: 40 mg (72%). Anal. Calcd for C$_4$N$_4$Au$_2$Zn: C, 8.53%; H, 0.00%; N, 9.94%. Found: C, 8.84%; H, 0.00%; N, 10.15%. IR (KBr. cm$^{-1}$): 2216 (w), 2198 (s), 2158 (w), 517 (m). A similar preparation (using a different stoichiometry) and the crystal structure have been previously reported.[20]

β-Zn[Au(CN)$_2$]$_2$ (13β). To a 3 mL acetonitrile solution containing Zn(NO$_3$)$_2$6H$_2$O (30 mg, 0.10 mmol), a 3 mL acetonitrile solution of [$^n$Bu$_4$N][Au(CN)$_2$] ½ H$_2$O (100 mg, 0.20 mmol) was added while stirring, yielding an immediate precipitate. The mixture was centrifuged, after which the solvent was removed and the powder allowed to dry overnight. The sample was washed with three portions of acetonitrile (6 mL) through filter paper to remove any KNO$_3$ or unreacted starting material. The resulting powder was air dried, yielding a white powder of β-Zn[Au(CN)$_2$]. (13β). Yield: 40 mg (72%). Anal. Calcd for C$_4$N$_4$Au$_2$Zn: C, 8.53%; H, 0.00%; N, 9.94%. Found: C, 8.51%; H, 0.00%; N, 9.78%. IR (KBr. cm$^{-1}$): 2221 (sh), 2199 (s), 2158 (w), 521 (m).

X-ray quality crystals of 13β can be grown by slow, partial, evaporation of a 20 mL methanol solution of KAu(CN)$_2$ (10 mL, 57 mg, 0.20 mmol) and Zn(ClO$_4$)$_2$ 6H$_2$O (10 mL, 37 mg, 0.10 mmol). The crystals and powder had identical IR spectra and powder diffractograms. Crystals of KClO$_4$ are interspersed with crystals of 13β.

γ-Zn[Au(CN)$_2$]$_2$ (13γ). Method 1: To a 1 mL acetonitrile solution containing Zn(ClO$_4$)$_2$ 6H$_2$O (37 mg, 0.10 mmol), a 1 mL acetonitrile solution of [$^n$Bu$_4$N][Au(CN)$_2$] ½ H$_2$O (150 mg, 0.30 mmol) was added dropwise while stirring, yielding an immediate precipitate. The mixture was centrifuged, after which the solvent was removed and the powder allowed to dry overnight. The sample was washed with three portions of acetonitrile (2 mL) through filter paper to remove any KClO$_4$ and unreacted starting material. The resulting powder was air dried, yielding a white powder of γ-Zn[Au(CN)$_2$]$_2$. (13γ). Yield: 40 mg (72%). Anal. Calcd for C$_4$N$_4$Au$_2$Zn: C, 8.53%; H, 0.00%; N, 9.94%. Found: C, 8.62%; H, 0.00%; N, 9.82%. IR (KBr. cm$^{-1}$): 2187 (s), 2149 (w), 526 (m).

Method 2: To a 5 mL (99:1) acetonitrile:water solution containing Zn(ClO$_4$)$_2$ 6H$_2$O (37 mg, 0.10 mmol), a 5 mL (99:1) acetonitrile:water solution of KAu(CN)$_2$ (57 mg, 0.20 mmol) was added dropwise while stirring, yielding an immediate precipitate, which was filtered and washed with three portions of acetonitrile (3 mL), leaving a powder of 13γ. Yield: 43 mg (77%). The IR spectra and X-ray powder diffractograms of the products from both methods are identical.

δ-Zn[Au(CN)$_2$]$_2$ (13δ). A 15 mL aqueous solution containing KAu(CN)$_2$ (114 mg, 0.40 mmol) and KCN (26 mg, 0.40 mmol) was covered with a watch glass and brought to a boil, after which HCl (0.80 mL, 0.100 N solution. 0.080 mmol) was added. The solution was cooled until the beaker was warm to the touch, after which a 15 mL aqueous solution of ZnCl$_2$ (26 mg, 0.20 mmol) was added. Over several hours, crystals of δ-Zn[Au(CN)$_2$]$_2$ (13δ) deposited. The crystals were immediately filtered and dried. Yield 60 mg (56%). Anal. Calcd for C$_4$N$_4$Au$_2$Zn: C, 8.53%; H, 0.00%; N, 9.94%. Found: C, 8.44%; H, 0.00%; N, 10.27%. IR (KBr. cm$^{-1}$): 2191 (s), 2188 (s), 2156 (w), 2151 (w), 526 (m). Further evaporation yields a mixture of 13α and 13δ crystals, after which a yellow powder of AuCN is produced.

{Zn(NH$_3$)$_2$[Au(CN)$_2$]$_2$} (14). Ammonia gas (10 mL), from the saturated headspace of a bottle of concentrated ammonia solution (29.4%), was introduced to a vial containing 20 mg of 13β. The vial was sealed and left standing for 30 min. yielding a white powder. The vial was then opened and the ammonia allowed to escape for 5 min. generating a bright, yellow powder of {Zn(NH$_3$)$_2$[Au(CN)$_2$]$_2$} 14. Anal. Calcd. for C$_4$H$_6$N$_6$Au$_2$Zn: C, 8.04%; H, 1.01%; N, 14.07%. Found: C, 8.30%; H, 0.91%; N, 13.87%. IR (KBr. cm$^{-1}$): 3290 (m), 3178 (w), 2158 (s), 2117 (sh), 1202 (s), 618 (br.m).

Using 13α, 13γ, or 13δ as the starting material still generated {Zn(NH$_3$)$_2$[Au(CN)$_2$]$_2$} 14.

If a sample of {Zn(NH$_3$)$_2$[Au(CN)$_2$]$_2$} 14 is left unsealed for an hour, a white powder of Zn[Au(CN)$_2$]$_2$ 13 forms. Anal, calcd. for C$_4$N$_4$Au$_2$Zn: C, 8.53%; H, 0.00%; N, 9.94%. Found: C, 8.86%; H, 0.00%; N, 9.80%. IR (KBr. cm$^{-1}$): 2197 (s), 2160 (w), 518 (m).

2.3.3 X-Ray Crystallographic Analysis

Crystallographic data for the four polymorphic compounds 13α-13β and {Zn(NH$_3$)$_2$[Au(CN)$_2$]$_2$} 14 are tabulated in Table 9. Crystals of 13β and 13δ were mounted on glass fibers using epoxy adhesive. 13β was a colourless plate having dimensions 0.20×0.20×0.02 mm$^3$ and 13δ was a colourless plate having dimensions 0.14×0.11×0.06 mm$^3$. The data for compounds 13β and 13δ were collected at room temperature on a Bruker Smart instrument with an APEX 11 CCD area detector at a distance of 6.0 cm from the crystal. A Mo Kα fine-focus sealed tube operated at 1.5 kW power (50 kV, 30 mA) was utilized for data collection. The following data ranges were recorded: 13β=4°<2θ<57°; 13δ=7<2θ<65°.

For compound 13β, a total of 776 frames were collected with a scan width of 0.5° in ω: all frames were collected with a 20 s exposure time. The frames were integrated with the Bruker SAINT software package. Data were corrected for absorption effects using a numerical face-indexed technique (SADABS) with a transmission range of 0.058-0.700. Final unit-cell dimensions were determined based on the refinement of the XYZ-centroids of 1969 reflections with ranges 4°<2θ<51°

Crystals of compound 13δ were determined to be two component non-merohedral twins (CELL_NOW) by an approximately 180° rotation about the [100] direction in real space. A total of 4079 frames were collected with a scan width of 0.5° in ω: all frames were collected with a 20 s exposure time. Frames were integrated with the Bruker SAINT software package using the appropriate twin matrix. Data were corrected for absorption effects (TWINABS) with a transmission range of 0.036-0.110. Final unit-cell dimensions were determined based on the refinement of the XYZ-centroids of 9904 reflections with ranges 7°<2θ<61°

The structures of compounds 13β and 13δ were solved in CRYSTALS[70] using direct methods (SIR92) and expanded using Fourier techniques. Diagrams were prepared using Cameron.[71]

The coordinates and anisotropic temperature factors for all atoms of compounds 13β and 13δ were refined. For 13β, the final refinement using observed data (I$_0$>2.50σ(I$_0$)) included an extinction parameter, and statistical weights included 103 parameters for 1656 unique reflections. For 13δ, the final refinement using observed data (I$_0$>2.50σ(I$_0$)) and statistical weights included 104 parameters for 2105 unique reflections. Selected bond lengths and angles are given in Tables 10 and 11 respectively.

X-ray powder diffractograms were collected on a Rigaku RAXIS rapid curved image plate area detector with a graphite monochromated Cu-Kα radiation source and a 0.5 μm collimator. Powder samples were adhered to a glass fiber with grease. Peak positions for 13γ and cell parameters were determined with Dicvol.[72] Structural models for 13γ were produced and refined with Powder Cell[73] using triclinic symmetry. The spacegroup and atomic positions of the carbon and nitrogen atoms were determined with CRYSTALS[70] using distance and angle restraints. A final refinement cycle for γ was conducted in PowderCell[73] in the tetragonal spacegroup P bar-4 b 2.

The powder pattern of $\{Zn(NH_3)_2[Au(CN)_2]_2\}$ 14 was compared with simulated patterns of the coordination polymer $\{Cd(NH_3)_2[Ag(CN)_2]_2\}$,[74] which was found to have a similar diffraction pattern. Unit cell determination and further refinements were performed in Powder Cell[73] using the atomic positions of the $\{Cd(NH_3)_2[Ag(CN)_2]_2\}$ complex.[74] The relative intensities of the 21/reflections for the observed powder pattern were consistently less intense and very broad then the intensities in the calculated powder diffractogram.

2.2.4 Synthesis and IR Spectra

Equations 1-4 below summarize schemes identified by the inventors for controlled synthesis of polymorphs 13α-13δ by the reaction of Zn(II) salts with two equivalents of the linear anionic $Au(CN)_2^-$ building block. All four materials have comparable elemental analyses and thus are true polymorphs, not pseudo-polymorphic solvent adducts. Elemental analysis indicated that when 13β was initially formed (eq 2), it contained at least one labile acetonitrile per $Zn[Au(CN)_2]_2$ unit. This complex readily desolvated when left in an unsealed container overnight. Powder X-ray diffractograms showed no difference between the solvated and desolvated forms of 13β.

Polymer 13 exhibits exquisite structural sensitivity to synthetic conditions. More particularly, the synthesis of each polymorph is sensitive to solvent choice,[75-79] concentration,[79] pH,[80, 81] and even the counterions associated with either the zinc(II) or gold(I) starting material, despite the fact that these counterions are not incorporated into the final polymer. This last point is best exemplified in the synthesis of 13β vs. 13γ (Equation 2 & 3), where changing the gold counterion from $K^+$ to $[^nBu_4N]^+$ and the zinc counterion from $NO_3^-$ to $ClO_4^-$ generates 13γ instead of 13β, under similar reaction conditions. Furthermore, if only one counterion is changed, a mixture of polymorphs 13β and 13γ are obtained. The counterions in the synthesis of 13β and 13γ could play an important role as a templating agent, preferentially inducing the formation of one network versus another.

Conversely, the synthetic route to 13α is insensitive to counterions and moderately insensitive to concentration, although mixtures of 13α and 13δ are formed under extremely concentrated conditions (2 mL total). Changing the solvent in equation 1 from water to methanol produces crystals of 13β only when $Zn(ClO_4)_2$ is used (See experimental section above). The difference may be partially attributed to changes in the hydrogen bonding characteristics of water vs. methanol.[82] The same effect is also observed in the synthesis of 13δ, which is done under acidic conditions (Equation 4) with $ZnCl_2$.

While the rationale behind the preferential formation of a particular polymer under a defined set of conditions is unclear, it is obvious (Equation 1-4) that the formation constant for each polymorph is relatively similar. Changing the solvent, concentration, counterion, and/or pH is sufficient to easily shift the resultant energy minimum from one polymorphic form to another.

$$ZnX_2 + 2\ KAu(CN)_2 \xrightarrow{30\ mL\ H_2O}_{X = Cl^-,\ NO_3^-,\ ClO_4^-} \alpha\text{-}Zn[Au(CN)_2]_{2(crystals)}\quad(1)$$

$$Zn(NO_3)_2 + 2\ [^nBu_4N][Au(CN)_2] \xrightarrow{1.\ 6\ mL\ CH_3CN}_{2.\ \text{-}CH_3CN\ (24\ h\ RT)} \quad(2)$$

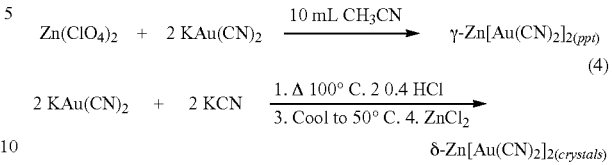

$$Zn(ClO_4)_2 + 2\ KAu(CN)_2 \xrightarrow{10\ mL\ CH_3CN} \gamma\text{-}Zn[Au(CN)_2]_{2(ppt)}\quad(4)$$

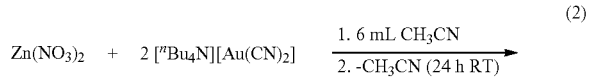

The IR spectra of all four polymorphs, 13α-13δ, are similar, having strong $\upsilon_{CN}$ stretches between 2187 and 2199 $cm^{-1}$ and readily visible $^{13}C$-satellites between 2158 and 2149 $cm^{-1}$. These bands are all shifted to higher energy relative to KAu(CN)$_2$ ($\upsilon_{CN}$=2141 $cm^{-1}$), indicating that all of the cyanide groups are bound to a zinc centre.[43] For the most part, the similarities in the IR spectra for 13α-13δ precluded the use of the IR signatures as a definitive polymorph identifier; this was accomplished on the basis of a combination of distinct crystal habit (FIG. 11), distinct X-ray powder diffractograms, and emission data (See below).

2.2.5 Crystal Structure of the Polymorphs

Crystal Structure of 13α. The synthesis, with a Zn:Au(CN)$_2$ ratio of 3:1, and the crystal structure of the resulting hexagonal crystals of $Zn[Au(CN)_2]_2$ (13α) were previously reported.[20] The inventors have determined that the stoichiometrically rational reaction of Zn(II) and two equivalents of KAu(CN)$_2$ in water generates the same hexagonal crystals (Table 10, FIG. 11); the crystal structure is briefly described below for comparative purposes. The crystal structure contains a zinc centre in a tetrahedral geometry, with four N-bound cyanides (Zn—N bond lengths of 1.939 and 1.978 Å), thereby generating a 3-D coordination polymer. The network structure of α consists of corner-sharing tetrahedra, analogous to SiO2-quartz (FIG. 12a);[83-87] each tetrahedron is defined by a gold(I) atom at each vertex and a zinc(II) atom at the centre. In order to efficiently utilize the large space between neighbouring zinc centres of this quartz-type net, the structure is six-fold interpenetrated (FIG. 12a—right).[85, 86] The interpenetration is supported via gold-gold bonds of alternating 3.11 and 3.16 Å. forming a 1-D zig-zag chain of $Au(CN)_2^-$ with an angle of 114.98° (FIG. 12b). A similar structure was reported for $Co[Au(CN)_2]_2$.[17]

Crystal Structure of 13β. Rectangular plate crystals of 13β (FIG. 11) were obtained from the partial evaporation of a methanol solution of $Zn(ClO_4)_2$ and $KAu(CN)_2$. Similar to the crystal structure of 13α, 13β also consists of a zinc(II) centre surrounded by 4 N-bound cyanide groups in a tetrahedral geometry with Zn—N bond lengths of 1.941 (14)-1.961 (14) Å (Table 11). The tetrahedra are corner-sharing, this time forming a 3-D structure that has a diamond-type topology;[82, 85, 86, 88-90] each building block in the network can be viewed as an adamantyl unit (FIG. 3a). The framework is analogous to cristobalite, another polymorph of $SiO_2$ (FIG. 3).[87] The 3-D networks in β are five-fold interpenetrated (FIG. 13b—right).[85, 86, 89] The interpenetrated networks are linked via gold-gold bonds ranging from 3.1471 (11)-3.2702 (6) Å and angles ranging from 104.951 (17)-180° (Table 11, FIG. 13c). Whereas the aurophilic array of α forms 1-D chains of Au-centres, the Au-array in β forms a 2-D (6.3)-network[85] in which the gold atoms form a distorted hexagonal motif array with gold atoms located at the vertices of the hexagons (FIG. 13c).

Crystal Structure of 13γ. Although single crystals of 13γ could not be obtained, pure microcrystalline powder of 13γ was synthesized from Zn(ClO$_4$): and [cation][Au(CN)$_2$] (cation=K$^-$."Bu$_4$N$^+$) in MeCN. The powder diffractogram of 13γ was observed to be similar to the previously reported Pb[Au(CN)$_2$]$_2$ structure.[126] Using this Pb(II) structure as a starting model, the structure of 13γ was determined from powder X-ray diffraction data. An excellent match between predicted and experimental powder diffractograms (FIG. 15) was obtained. The structure is both chemically reasonable and spectroscopically consistent. Interestingly, the crystal structure of 13γ has the same network structure as 13β; a diamond-type array formed by fused adamantyl units (FIGS. 13a and 13b).[82, 85, 86, 88-90] There are several differences between these polymorphs. Firstly, the networks of 13γ are four-fold interpenetrating (FIG. 14b) while 13β contains five independent networks (FIG. 13c).[85, 89] The interpenetration in 13γ is supported by gold-gold bonds of 3.29 Å. However, while a 2-D array of gold atoms is present in β, the gold atoms in 13γ primarily form dimers. Long gold-gold interactions of 3.58 Å link the dimers to one another (FIG. 14b). In addition, the shape of the diamond network in 13γ is more prolate than that of 13β. A single adamantyl framework in 13β has the dimensions 25.8×16.5×13 Å (FIG. 3a) while the adamantyl framework in 13γ has the dimensions 33.8×9.6×9.6 Å.

Crystal Structure of 13δ. Twinned cross-shaped crystals of 13δ (FIG. 11) were obtained from an acidic aqueous solution of ZnCl$_2$. KAu(CN)$_2$ and KCN; this synthesis was modified from an old report of Zn/Au(CN)$_2$ reactivity that did not identify any of the polymorphs.[91] As in 13α-13γ, the crystal structure of 13δ contains a tetrahedral zinc centre with Zn—N (cyano) bond lengths ranging from 1.956 (10) to 1.986 (10) Å. However, while 13α, 13β, and 13γ form easily recognizable structures based on corner-sharing tetrahedra, the 3-D structure of 13δ is considerably more complicated. Temporarily omitting one of the Au(CN)$_2^-$ units on each zinc (the Au(CN)$_2^-$ unit formed by Au(3)). the structure can be simplified to a corrugated 2-D (6.3)-herringbone structure (FIGS. 16a & 16b) along the (10-1) plane.[85, 88] A second (6.3)-herringbone network is interwoven through the first (FIG. 16b—right). Long gold-gold distances of 3.6430 (9) Å represent the only close contact between this pair of networks. Via the previously omitted Au(CN)$_2^-$ unit, each individual herringbone network is linked to four additional networks (FIG. 16c—left)—the pair of interwoven networks above, and the pair of networks below—completing the basic 3-D structure. The void space is filled by two additional identical 3-D interpenetrated networks (FIG. 16c—right).[85] The interpenetration is supported via gold-gold bonds of 3.3318 (4) and 3.3382 (5) Å (FIG. 16d). The gold-gold bonds in δ are longer then those observed in 13α, 13β, and 13γ.

Polymorphism has been extensively investigated in coordination polymers, with structural differences between polymorphic forms attributed to connectivity, interpenetration, and degree of solvent inclusion (pseudo-polymorphism).[58, 78, 88, 92-94] Even the widely investigated prototypical Prussian Blue-like system. Mn[Fe(CN)$_6$], has been observed in two polymorphic forms: the standard rock-salt structure, and the doubly interpenetrated form.[95]

In the case of the four polymorphs 13α-13δ all have a zinc centre in a tetrahedral geometry. The difference between the networks of 13α and 13δ, and the diamond-like networks of 13β and 13γ is due to the pathway connecting zinc centres. Furthermore, the four polymorphs differ in the degree of interpenetration. decreasing from six to three from 13α to 13δ respectively. In all of the polymers the interpenetration is supported by gold-gold bonds ranging from 3.11-3.34 Å. While it is generally believed that a lower degree of interpenetration is ideal for creating empty cavities,[82] it is interesting to note that 13β has a significantly lower density then the other polymorphs, despite the relatively high degree of interpenetration.[48, 96, 97]

2.2.6 Thermal Stability

All four polymorphs are stable until at least 350° C., after which they begin to decompose, losing all of the cyanide groups in one step between 350-390° C. Thus, despite the different levels of interpenetration and supporting gold-gold networks, the four polymorphs show very similar thermal stabilities. In addition, DSC measurements of 13α-13δ over the range 25-300° C. show no indication of a phase change from one polymorph to another.

2.2.7 Photoluminesence

Gold (II) centres which are separated by less then 3.6 Å (the sum of the Van der Waals radii for gold)[98] are said to show gold-gold (aurophilic) bonding;[99] such systems are known to be potentially luminescent. As a result of their interesting emission properties, compounds containing gold-gold bonds have received a great deal of attention.[100-103] In the crystal structures of 13α-13δ, network interpenetration is supported via gold-gold bonds on the order of 3.11-3.34 Å and indeed. 13α-13γ are emissive when exposed to UV light at room temperature.

The photoluminescence spectra of 13α-13δ are summarized in Table 12. Compound 13α shows two emission bands at 390 and 480 nm (FIG. 17) at room temperature. The excitation spectra show an identical excitation maximum at 345 nm for both emission bands (FIG. 17 bottom), However, for crystals, or densely packed powder samples of 13α, the 480 nm emission band can be directly excited at 390 nm with a concomitant change in the relative intensities of the 390 and 480 nm emissions. The lifetimes of both emission energies were measured in order to determine the nature of the emission. The 390 nm emission has a lifetime of 240 ns while the 480 nm emission has a lifetime of 930 ns. Based on this data and the lifetimes of other Au(CN)$_2^-$-based coordination polymers.[104-105] the 390 and 480 nm emissions are assigned to a singlet (flouresence) and triplet (phosphoresence) emission respectively. Due to the large spin-orbit coupling of gold, phosphoresence is generally the predominant emission pathway. The presence of both types of emission, as in 13α, is less common.[105]

In contrast, 13β and 13γ show only one emission band with similar energies at 450 and 440 nm respectively (Table 12, FIG. 17). For 13δ, despite the presence of gold-gold bonds, hand-picked single crystals of δ showed no observable room temperature luminescence. The absorption spectra of 13α-13γ showed that the lowest energy absorption band is consistent with the lowest fluorescence excitation energy, confirming that the observed emissions are attributed to the polymorphs. Other Au(CN)$_2^-$-based coordination polymers have also shown excitation and emission energies in this range.[100, 103, 106]

It has been observed both theoretically and experimentally that the gold-gold distances in a structurally related series of metal-metal bonded gold(I) systems are inversely proportional to the emission energies. Indeed, the low energy, phosphoresence, emissions of 13α-13γ obey this trend; on average, shorter gold-gold bonds in a (3.11 and 3.16 Å) emit at lower energy than the gold-gold bonds in 13β (3.1471 (11)-3.2702 (6) Å) and 13γ (3.29 Å). A plot of average Au—Au distance vs. emission energy yields a straight line and also predicts that 13δ should emit at around 427 nm. However, a non-emissive decay pathway may be more prevalent in 13δ at room temperature, rendering it truly non-emissive.

2.2.8 Response to Ammonia Exposure

Based on the sensitive and dramatic visible and IR spectral response of the related $Cu[Au(CN)_2]_2(H_2O)_2$ system to ammonia gas as described above, the response of the colourless polymorphs 13α-13δ to ammonia vapour was examined, with particular focus on possible emission changes acting as a sensory output. Ammonia detectors have a variety of applications in agriculture, the automotive industry, industrial refrigeration, medical diagnosis, and anti-terrorism.[107] From a health perspective, the human nose is capable of sensing ammonia at a concentration of 50 ppm, but the permissible long term exposure limit of ammonia is below this, at 20 ppm.[107, 108] For these reasons, the design of materials for the detection of ammonia is of great interest.

When the four polymorphs 13α-13δ were exposed to a large excess of $NH_3$ gas, a new white powder was formed, the IR spectrum of which contained only one $\upsilon_{CN}$ band at 2141 cm$^{-1}$, indicative of free $Au(CN)_2^-$ units. The IR spectrum also showed the presence of metal-bound ammonia.[109] suggesting that the zinc(II) centre is either tetrahedral, coordinated by four ammonia units, or octahedral, coordinated by six ammonia units; the former is more likely on the basis of typical Zn(II)-ammine coordination chemistry[110-112] and thus this ammonia-saturated powder is tentatively formulated as $\{Zn(NH_3)_4[Au(CN)_2]_2\}$ 15. The room temperature luminescence spectrum of this ammonia-saturated complex shows a single emission peak at 430 nm with an excitation band at 365 nm (FIG. 19). Unfortunately, rapid loss (seconds) of some of the ammonia occurs when the sample is unsealed, precluding further structural or elemental analysis.

Removal from the ammonia-rich atmosphere and subsequent rapid loss of excess ammonia from $\{Zn(NH_3)_4[Au(CN)_2]_2\}$ 15 generates a yellow powder (FIG. 18), which is stable in the absence of ammonia for 30 minutes. Elemental analysis of this yellow powder is consistent with a bis-ammonia adduct of $Zn[Au(CN)_2]_2$ 13, namely $\{Zn(NH_3)_2[Au(CN)_2]_2\}$ 14. The IR spectrum of $\{Zn(NH_3)_2[Au(CN)_2]_2\}$ 14 shows a single $\upsilon_{CN}$ band at 2158 cm$^{-1}$, suggesting that all of the $Au(CN)_2^-$ units occupy a similar environment. Furthermore, the vibrational modes associated with the ammonia molecule suggest a metal-bound ammine is present.[109] Comparison of the powder X-ray diffractogram of $\{Zn(NH_3)_2[Au(CN)_2]_2\}$ 14 to other closely related bis-ammonia coordination polymers[113] reveals a similar diffractogram to both $\{Cd(NH_3)_2[Ag(CN)_2]_2\}$[74] and $\{Cu(NH_3)_2[Ag(CN)_2]_2\}$.[114] The powder pattern of the cadmium polymer is a better fit, which is consistent with the fact that both zinc(II) and cadmium(II) do not contain the Jahn-Teller axis present in the copper(II) system. Using the Cd-system as a starting model, the solid-state structure of $\{Zn(NH_3)_2[Au(CN)_2]_2\}$ was determined by fitting atomic coordinates to the experimental powder X-ray diffraction pattern. A good match was obtained (FIG. 20), except for the {211} reflections. These planes intersect Zn atoms, making them sensitive to $NH_3$ gain/loss, and are thereby much broader in comparison with the remaining peaks. Consistent with the IR data, the structure contains an octahedral zinc centre in $D_{4h}$ geometry having trans-ammonia molecules and four N-bound cyanides. Linking through the $Au(CN)_2^-$ units, the zinc centres form a 2-D corrugated sheet (FIG. 21a).[85, 86] with $Au(CN)_2^-$ units at the apex of the corrugation.[74] Additional parallel sheets stack via gold-gold bonds of 3.06 Å (FIG. 21b—left). Rather then forming chains or sheets of gold-gold bonds as in 13α, 13β and 13δ, only discrete dimers of $Au(CN)_2^-$ units are found, similar to 13γ. A second set of sheets are inclined and interpenetrated through the aforementioned parallel sheets.[85] These perpendicular sheets show no close gold-gold bonds or other interactions to one another. Room temperature photoluminescence of $\{Zn(NH_3)_2[Au(CN)_2]_2\}$ 14 shows a single emission band at 500 nm with an excitation at 400 nm (FIG. 19), which also matches the Au—Au distance/energy correlation graph.

The TGA of $\{Zn(NH_3)_2[Au(CN)_2]_2\}$ 14 shows a drop starting at room temperature and ending at 95° C. The mass loss is consistent with a loss of two equivalents of ammonia (% loss observed 6%; calculated 5.7%). As the temperature is increased a second loss from 350 to 390° C. is observed, consistent with decomposition of the polymer via cyanide loss and formation of ZnO and Au (% loss observed 15.2%; calculated 14.7%), as seen for 13α-13δ. However, this ammonia loss also occurs without heating: if $\{Zn(NH_3)_2[Au(CN)_2]_2\}$ 14 is left open to air for 30 minutes all ammonia molecules are released, leaving behind a white powder of $Zn[Au(CN)_2]_2$ 13. Interestingly, the X-ray powder diffractogram of this ammonia-free product indicated that a mixture of both 13α and 13δ polymorphs had been generated. However, the ratio of the two polymorphs is sample-dependent: cases ranging from pure 13α to pure 13δ and various ratios in between have all been observed (the controlling factor remains unclear). Photoluminescence spectra of the mixtures is consistent with the luminescence of 13α, and mixtures of 13α and non-emissive 13δ. It is important to note that reintroduction of ammonia vapour to any mixture of 13α:13δ, or even to pure δ, invariably regenerates the saturated $\{Zn(NH_3)_4[Au(CN)_2]_2\}$ 15 complex, followed by the bis-ammonia complex $\{Zn(NH_3)_2[Au(CN)_2]_2\}$ 14 (as confirmed by powder X-ray diffraction measurements in situ) upon removal of the ammonia-rich atmosphere.

In order to probe the mechanism of adsorption/desorption,[115] titration of all four polymorphs with sequential equivalents of $NH_3$, monitoring the $\upsilon_{CN}$ stretch in the IR, was investigated. Titration of 13α and 13δ reveals that they bind ammonia in a stepwise fashion (Equation 5), first converting to $\{Zn(NH_3)_2[Au(CN)_2]_2\}$ 14 ($\upsilon_{CN}$ 2158 cm$^{-1}$) and then to $\{Zn(NH_3)_4[Au(CN)_2]_2\}$ 15 ($\upsilon_{CN}$ 2141 cm$^{-1}$). This reaction is completely reversible; i.e., loss of ammonia regenerates the same polymorph. However, titration of 13β and 13γ reveals that the tetraaminezinc(II) complex forms directly (Equation 6), with no intermediate of $\{Zn(NH_3)_2[Au(CN)_2]_2\}$ observed. Apparently, sufficient ammonia must be present to break all the bonds between the zinc(II) and the four cyanides in order for initial $NH_3$-uptake to occur. Due to the adsorption routes for the four polymorphs, it is clear that once $\{Zn(NH_3)_4[Au(CN)_2]_2\}$ is formed from 13β and 13γ, these polymorphs cannot be regenerated upon $NH_3$-desorption; mixtures of 13α and 13δ are produced instead.

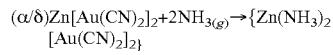
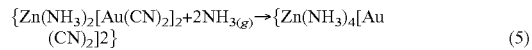

(5)

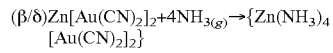
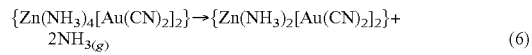

(6)

Porosity measurements on all four polymorphs showed no adsorption of nitrogen gas at 77 K. Despite this, 13α-13δ reversibly bind ammonia vapour. It is well-known that non-porous coordination polymers can be quite flexible in the solid-state.[54, 116, 117] The d$^{10}$ zinc(II) cation can adopt several geometries encompassing coordination numbers from two to six;[102, 118] undoubtedly, this flexibility facilitates the structural rearrangement which occurs as the ammonia interacts with the zinc(II) centre. Note that although $NH_3$-binding occurs at Zn(II), it is the array of $Au(CN)_2^-$ units that act as the sensor, as the structural rearrangement changes the gold-gold distance and thus the emission energy.

As discussed above, ammonia sensors are used in a wide range of settings.[107] For each application there are different requirements for an ideal sensor, including detection limits (0.1 ppb-200 ppm), response times (seconds-minutes), and operating temperatures (0-500° C.).[107] Due to the highly varying requirements there are several different types of sensors employed in the detection of ammonia. Some common ammonia-sensor materials include conducting compounds based on metal-oxides[119-121] or polymers such as polypyrrole[122] and polyaniline;[123] other sensors are based on spectrophotometric determination.[124, 125] While metal oxide-based sensors are very common, they require a high operating temperature, making them unsuitable in some applications, e.g. medical diagnostics.[107] Conversely, although atomic absorption-based sensing can be operated at room temperature with high sensitivity, it is extremely expensive.[107]

This example clearly shows that all four polymorphs of zinc polymer 13 act as vapoluminescent sensors for ammonia. However, in order to determine if the $Zn[Au(CN)_2]_2$ materials (which are relatively inexpensive and quite stable) could compete with current $NH_3$-detection systems, quantitative detection limits for each polymorph were measured, by monitoring the intensity of the $\{Zn(NH_3)_2[Au(CN)_2]_2\}$ emission band ($\lambda_{max}$=500 nm, $\lambda_{max}$=400 nm) emission band at 520 nm. Although sensitivities of the polymers vary depending on polymorph, the lowest detection limit was observed for 13β, with a $NH_3$-detection limit of 1 ppb. The response times are also fast: within seconds for all polymorphs. In comparison with other materials used as ammonia sensors, these four coordination polymers have some of the lowest $NF_3$-detection limits and response times.

In summary, the reaction of various zinc salts with the linear, anionic $Au(CN)_2^-$ bridging ligand formed four structurally unique polymorphs, three of which are luminescent at room temperature. Care must be taken when synthesizing these polymorphs since changing the concentration, counterion, pH, and/or solvent can redirect the synthesis from one polymorphic form to another. All four polymorphs reversibly act as very sensitive sensors for ammonia vapour, changing their emission energies as ammonia is bound. The emission can be correlated to the gold-gold array distance in each compound.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

TABLE 1

Crystallographic Data and Structural Refinement Details

|  | 1 (Green) | 2 (Blue) | 3 | 4 |
|---|---|---|---|---|
| empirical formula | $C_8H_{12}N_4Au_2CuO_2S_2$ | $C_8H_{12}N_4Au_2CuO_2S_2$ | $C_7H_7N_5Au_2CuO$ | $C_{14}H_{10}N_6Au_2Cu$ |
| fw | 717.82 | 717.82 | 634.65 | 719.76 |
| Crystal system | monoclinic | triclinic | monoclinic | monoclinic |
| Space group | C2/c | P$\bar{1}$ | C2/c | P2$_1$/c |
| a. Å | 11.5449(15) | 7.874(7) | 12.8412(10) | 7.3438(7) |
| b. Å | 14.191(4) | 12.761(11) | 14.5056(8) | 14.1201(10) |
| c. Å | 11.5895(12) | 16.207(13) | 13.9932(9) | 8.2696(6) |
| α. deg | 90 | 89.61(7) | 90 | 90 |
| β. deg | 112.536(9) | 82.29(7) | 96.064(3) | 94.082(3) |
| γ. deg | 90 | 88.57(7) | 90 | 90 |
| V. Å$^3$ | 1753.8(6) | 1613.2(24) | 2591.9(3) | 855.34(12) |
| Z | 4 | 2 | 8 | 4 |
| T. K | 293 | 293 | 293 | 293 |
| λ. Å | 0.70930 | 1.54180 | 1.54180 | 1.54180 |
| $\rho_{calcd}$. g · cm$^{-3}$ | 2.719 | 2.955 | 3.253 | 2.794 |
| μ. mm$^{-1}$ | 18.079 | 37.500 | 43.542 | 33.103 |
| $R_1^a$ (I > xσ(I))$^b$ | 0.042 | 0.062 | 0.032 | 0.028 |
| $wR_2^a$ (I > xσ(I))$^b$ | 0.047 | 0.082 | 0.046 | 0.040 |
| Goodness of fit | 2.20 | 1.38 | 0.93 | 1.00 |

$^a$Function minimized $\Sigma w(|F_o| - |F_c|)^2$ where $w^{-1} = \sigma^2(F_o) + 0.0001F_o^2$, $R = \Sigma||F_o| - |F_c||/\Sigma|F_o|$, $R_w = [\Sigma w|F_o| - |F_c|)^2/\Sigma w|F_o|^2)^{1/2}$.
$^b$For 1, x = 2.5; for 2, 3 and 4, x = 3.

TABLE 2

Selected bond lengths (Å) and angles (°) for $Cu[Au(CN)_2]_2(DMSO)_2$ (1).

| Au(1)—Au(2) | 3.22007(5) | Cu(1)—N(2) | 2.107(18) |
|---|---|---|---|
| Cu(1)—O(1) | 1.949(7) | Cu(1)—N(3) | 1.965(11) |
| O(1)—Cu(1)—O(1*) | 167.0(6) | Cu(1)—N(2)—C(2) | 180 |
| O(1)—Cu(1)—N(2) | 96.5(3) | Cu(1)—N(3)—C(3) | 178.6(12) |
| O(1)—Cu(1)—N(3) | 87.3(4) | Au(2)—Au(1)—Au(2) | 171.73(3) |
| O(1*)—CU(1)—N(3) | 88.4(4) | Au(1)—N(1)—C(1) | 180 |
| N(2)—Cu(1)—N(3) | 109.5(4) | Au(1)—N(2)—C(2) | 180 |
| N(3)—Cu(1)—N(3*) | 140.9(8) | Au(2)—N(3)—C(3) | 178.9(12) |
| Cu(1)—O(1)—S(1) | 127.2(6) | C(1)—Au(1)—C(2) | 180 |

Symmetry transformations:
*−x + 1, y, −z + ½;
'−x + ½, −y − 5/2, z + 1.

TABLE 3

Selected bond lengths (Å) and angles (°) for Cu[Au(CN)$_2$]$_2$(DMSO)$_2$ (2).

| | | | |
|---|---|---|---|
| Au(1)—Au(2) | 3.419(3) | Au(3)—Au(4) | 3.592(4) |
| Cu(1)—O(1) | 2.02(3) | Cu(2)—O(3) | 1.97(3) |
| Cu(1)—O(2) | 1.95(3) | Cu(2)—O(4) | 2.29(3) |
| Cu(1)—N(11) | 2.42(4) | Cu(2)—N(12) | 2.11(4) |
| Cu(1)—N(21) | 1.97(4) | Cu(2)—N(22) | 2.37(5) |
| Cu(1)—N(31) | 2.42(4) | Cu(2)—N(32) | 2.03(5) |
| Cu(1)—N(41) | 1.99(4) | Cu(2)—N(42) | 2.00(5) |
| O(1)—Cu(1)—O(2) | 95.2(12) | O(3)—Cu(2)—O(4) | 93.0(12) |
| O(1)—Cu(1)—N(11) | 85.9(12) | O(3)—Cu(2)—N(12) | 87.8(15) |
| O(2)—Cu(1)—N(11) | 86.4(12) | O(4)—Cu(2)—N(12) | 87.0(14) |
| N(11)—Cu(2)—N(21) | 92.7(14) | N(12)—Cu(2)—N(22) | 92.3(16) |
| N(11)—Cu(2)—N(31) | 172.7(13) | N(12)—Cu(2)—N(32) | 172.0(17) |
| N(11)—Cu(2)—N(41) | 92.6(14) | N(12)—Cu(2)—N(42) | 95.2(17) |
| N(21)—Cu(2)—N(31) | 92.6(15) | N(22)—Cu(2)—N(32) | 91.4(17) |
| N(21)—Cu(2)—N(41) | 90.7(15) | N(22)—Cu(2)—N(42) | 91.2(17) |
| N(31)—Cu(2)—N(41) | 92.3(14) | N(32)—Cu(2)—N(42) | 91.8(18) |
| Cu(1)—O(1)—S(1) | 124.9(17) | Cu(2)—O(3)—S(3) | 125.4(20) |
| Cu(1)—O(2)—S(2) | 124.4(19) | Cu(2)—O(4)—S(4) | 127.9(18) |
| Cu(1)—N(11)—C(11) | 169.2(45) | Cu(2)—N(12)—C(12) | 163.5(50) |
| Cu(1)—N(21)—C(21) | 163.5(41) | Cu(2)—N(22)—C(22) | 159.5(46) |
| Cu(1)—N(31)—C(31) | 161.7(43) | Cu(2)—N(32)—C(32') | 174.6(45) |
| Cu(1)—N(41)—C(41) | 166.4(33) | Cu(2)—N(42)—C(42) | 170.0(45) |
| C(11)—Au(1)—C(12) | 172.7(25) | C(31)—Au(3)—C(32) | 172.6(18) |
| C(21)—Au(2)—C(22*) | 175.9(23) | C(41[b])—Au(4)—C(42) | 177.9(20) |
| Au(1)—C(11)—N(11) | 175.8(50) | Au(3)—C(31)—N(31) | 171.0(39) |
| Au(1)—C(12)—N(12) | 175.3(58) | Au(3)—C(32)—N(32[b]) | 175.6(49) |
| Au(2)—C(21)—N(21) | 173.2(42) | Au(4[b])—C(41)—N(41) | 174.2(38) |
| Au(2*)—C(22)—N(22) | 175.2(56) | Au(4)—C(42)—N(42) | 170.1(46) |

Symmetry transformations:
*−x + 1, −y + 1, −z + 1;
*[b]−x + 1, −y, −z + 1;
'x + 2, y, z − 1;
[b]x − 2, y, z + 1.

TABLE 4

Selected bond lengths (Å) and angles (°) for Cu[Au(CN)$_2$]$_2$(DMF) (3).

| | | | |
|---|---|---|---|
| Au(1)—Au(1*[a]) | 3.3050(12) | Cu(1)—N(2) | 1.990(11) |
| Au(2)—Au(2*[b]) | 3.1335(13) | Cu(1)—N(3) | 1.961(10) |
| Cu(1)—O(1) | 2.202(12) | Cu(1)—N(4[b]) | 1.982(10) |
| Cu(1)—N(1') | 1.958(10) | O(1)—C(5) | 1.202(17) |
| N(1[a])—Cu(1)—N(2) | 89.8(4) | C(1)—Au(1)—C(2) | 176.0(6) |
| N(1[a])—Cu(1)—N(3) | 88.7(5) | C(3)—Au(2)—C(4) | 175.4(6) |
| N(4[b])—Cu(1)—N(2) | 89.6(5) | Cu(1[c])—N(1)—C(1) | 170.1(12) |
| N(4[b])—Cu(1)—N(3) | 89.3(5) | Cu(1)—N(2)—C(2) | 172.7(14) |
| N(1[a])—Cu(1)—N(4[b]) | 166.7(5) | Cu(1)—N(3)—C(3) | 170.8(12) |
| N(2)—Cu(1)—N(3) | 169.2(5) | Cu(1[d])—N(4)—C(4) | 172.1(12) |
| O(1)—Cu(1)—N(1[a]) | 95.1(5) | Au(1)—C(1)—N(1) | 174.9(13) |
| O(1)—Cu(1)—N(2) | 98.3(5) | Au(1)—C(2)—N(2) | 177.8(14) |
| O(1)—Cu(1)—N(3) | 92.4(5) | Au(2)—C(3)—N(3) | 174.3(13) |
| O(1)—Cu(1)—N(4[b]) | 98.1(5) | Au(2)—C(4)—N(4) | 177.5(16) |
| Cu(1)—O(1)—C(5) | 125.4(13) | | |

Symmetry transformations:
*[a]−x − 1, y, −z + 3/2;
*[b]−x − 1, y, −z + 1/2;
[a]x, −y, z − 1/2;
[b]x, −y − 1, z + 1/2;
[c]x, −y, z + 1/2;
[d]x, −y − 1, z − 1/2.

TABLE 5

Selected bond lengths (Å) and angles (°) for Cu[Au(CN)$_2$]$_2$(pyridine)$_2$ (4).

| | | | |
|---|---|---|---|
| Cu(1)—N(1) | 2.016(9) | Cu(1)—N(3) | 2.007(7) |
| Cu(1)—N(2*[a]) | 2.532(9) | | |
| N(1)—Cu(1)—N(2*[a]) | 89.5(4) | C(2)—Au(1)—C(1) | 177.8(4) |
| N(1')—Cu(1)—N(2*[a]) | 90.5(4) | Cu(1)—N(1)—C(1) | 169.7(9) |
| N(1)—Cu(1)—N(3) | 90.0(3) | Cu(1*[b])—N(2)—C(2) | 173.3(9) |
| N(1)—Cu(1)—N(3') | 90.0(3) | Au(1)—C(1)—N(1) | 177.9(9) |
| N(2*[a])—Cu(1)—N(3) | 90.4(3) | Au(1)—C(2)—N(2) | 177.2(11) |
| N(2*[a])—Cu(1)—N(3') | 89.6(3) | | |

Symmetry transformations:
*[a]x − 1, −y + 1/2, z − 1/2;
*[b]x + 1, −y + 1/2, z + 1/2;
'−x + 1, −y, −z + 1.

TABLE 6

Maximum Solid-state Visible Reflectance (nm) and Cyanide $v_{CN}$ Absorptions (cm$^{-1}$) for Different Cu[Au(CN)$_2$]$_2$(solvent)$_x$ Complexes

| Complex | Maximum visible reflectance | $v_{CN}$ absorption(s) From solution | From adsorption[a] |
|---|---|---|---|
| (1) Cu[Au(CN)$_2$]$_2$(DMSO)$_2$ | 550 ± 7 | 2183 (s), 2151 (s) | 2184 (s), 2151 (s) (from 5) |
| (2) Cu[Au(CN)$_2$]$_2$(DMSO)$_2$ | 535 ± 15 (broad) | 2206 (m), 2193 (s), 2175 (m), 2162 (m) | — |

TABLE 6-continued

Maximum Solid-state Visible Reflectance (nm) and Cyanide $v_{CN}$ Absorptions (cm$^{-1}$) for Different Cu[Au(CN)$_2$]$_2$(solvent)$_x$ Complexes

| Complex | Maximum visible reflectance | $v_{CN}$ absorption(s) From solution | From adsorption[a] |
|---|---|---|---|
| (3) Cu[Au(CN)$_2$]$_2$(DMF) | 498 ± 7 | 2199 (s) | 2199 (s) |
| (4) Cu[Au(CN)$_2$]$_2$(pyridine)$_2$ | 480 ± 15 (broad) | 2179 (m), 2167 (s), 2152 (m), 2144 (m) | 2179 (m), 2167 (s), 2152 (m), 2144 (m) |
| (5) Cu[Au(CN)$_2$]$_2$(H$_2$O)$_2$ | 535 ± 5 | 2217 (s), 2194 (w), 2172 (s) | 2217 (s), 2194 (w), 2171 (s) (from 1) 2216 (s), 2196 (w), 2171 (s) (from 2) |
| (6) Cu[Au(CN)$_2$]$_2$ | 560 ± 20 (v. broad) | 2191 (s) | — |
| (7) Cu[Au(CN)$_2$]$_2$(CH$_3$CN)$_2$ | — | 2297 (w), 2269 (w), 2191 (s) | |
| (8) Cu[Au(CN)$_2$]$_2$(dioxane)(H$_2$O) | 505 ± 15 (broad) | 2201 (s), 2172 (w) | 2200 (s), 2174 (w) |
| (9) Cu[Au(CN)$_2$]$_2$(NH$_3$)$_4$ | 433 ± 7 | — | 2175 (m), 2148 (s) |

[a]All solvent adducts were made from 2 unless specified

TABLE 7

Thermal Decomposition of Different Cu[Au(CN)$_2$]$_2$(solvent)$_x$ Complexes

| Complex | Temperature (° C.) | Decomposition product or lost fragment | Weight (%) calcd | Weight (%) found |
|---|---|---|---|---|
| 3 | 195-280 | -DMF | 11.5 | 13.6 |
|   | 310-355 | $-2C_2N_2 + O$ | 13.8 | 11.5 |
|   | 400 | CuO + 2Au | 74.6 | 73.9 |
| 4 | 155-190 | −1pyridine | 11.0 | 10.9 |
|   | 210-260 | −1pyridine | 11.0 | 12.6 |
|   | 310-330 | $-2C_2N_2 + O$ | 12.2 | 9.2 |
|   | 400 | CuO + 2Au | 65.8 | 66.4 |
| 5 | 140-180 | −2water | 6.0 | 5.5 |
|   | 260-380 | $-2C_2N_2 + O$ | 14.7 | 13.5 |
|   | 400 | CuO + 2Au | 79.2 | 81.5 |
| 6 | 200-350 | $-2C_2N_2 + O$ | 15.2 | 15.5 |
|   | 400 | CuO + 2Au | 81.7 | 80.9 |
| 8 | 150-280 | -dioxane-H$_2$O | 15.9 | 17.5 |
|   | 290-330 | $-2C_2N_2 + O$ | 13.2 | 10.3 |
|   | 400 | CuO + 2Au | 70.9 | 71.1 |
| 9 | 50-95 | −1NH$_3$ | 2.7 | 2.8 |
|   | 115-220 | −3NH$_3$ | 8.1 | 7.5 |
|   | 280-350 | $-2C_2N_2 + O$ | 14.0 | 13.7 |
|   | 400 | CuO + 2Au | 75.2 | 74.4 |

TABLE 8

List of Selected VOCs that 1 can Detect, Spectral Data, and Its Sensitivity

| VOC | $v_{CN}$ for 1 (solvent)/ excess | $\lambda_{max}$ (nm)/ excess | Response time at saturation | Minimum detectable concentration by IR | $v_{CN}$ for 1 (VOC) at sensitivity limit | Minimum detectable concentration by visible reflectance | $\lambda_{max}$ (nm) at sensitivity limit | Reversible without Heating |
|---|---|---|---|---|---|---|---|---|
| Compound 1 | 2216, 2171 | 532 | N/A | N/A | N/A | N/A | N/A | N/A |
| Ammonia | 2141, 2136 | 435 | <5 s | 36 ppb | 2181, 2151 | 230 ppb | 510 | No |
| Methylamine | 2139 | 438 | <8 s | 120 ppb | 2188, 2139 | 360 ppb | 495 | No |
| Propylamine | 2143 | 428 | <10 s | 140 ppb | 2185, 2155 | 320 ppb | 502 | No |
| Butylamine | 2141 | 460 | 2 min | 100 ppm | 2141 | 860 ppm | 468 | No |
| Diethylamine | 2144 | 478 | 10 min | 600 ppm | 2144 | 1600 ppm | 483 | No |
| Trimethylamine | Not sensitive | Not sensitive | N/A | N/A | N/A | N/A | Not sensitive | N/A |
| Ethylenediamine | 2141 | 408 | 10 s | 385 ppb | 2141 | 720 ppb | 415 | No |
| Pyridine | 2140, 2133 | 485 | 8 min | 400 ppm | 2193, 2148, 2142 | 875 ppm | 490 | Yes |
| Acetonitrile | 2297, 2269, 2192 | Broad | 10 min | 470 ppm | 2304, 2266, 2192 | 1120 ppm | Broad | Yes |
| DMF | 2199, 2171 | 482 | 12 min | 450 ppm | 2199, 2171 | 1155 ppm | 488 | Yes |

TABLE 8-continued

List of Selected VOCs that 1 can Detect, Spectral Data, and Its Sensitivity

| VOC | $\nu_{CN}$ for 1 (solvent)/ excess | $\lambda_{max}$ (nm)/ excess | Response time at saturation | Minimum detectable concentration by IR | $\nu_{CN}$ for 1 (VOC) at sensitivity limit | Minimum detectable concentration by visible reflectance | $\lambda_{max}$ (nm) at sensitivity limit | Reversible without Heating |
|---|---|---|---|---|---|---|---|---|
| DMSO | 2194, 2176, 2162 | 485 | 13 min | 1000 ppm | 2194, 2176, 2162 | 1640 ppm | 485 | Yes |

TABLE 9

Crystallographic Data for 13α-13δ and {Zn(NH$_3$)$_2$[Au(CN)$_2$]$_2$} 14

| | α[a] | β | γ[b] | δ | {Zn(NH$_3$)$_2$[Au(CN)$_2$]$_2$}[b] |
|---|---|---|---|---|---|
| empirical formula | C$_4$N$_4$Au$_2$Zn | C$_4$N$_4$Au$_2$Zn | C$_4$N$_4$Au$_2$Zn | C$_4$N$_4$Au$_2$Zn | C$_4$H$_6$N$_6$Au$_2$Zn |
| formula weight | 563.40 | 563.40 | 563.40 | 563.40 | 597.45 |
| crystal system | hexagonal | monoclinic | tetragonal | monoclinic | tetragonal |
| space group | P6$_4$2$_2$ | C2/c | P4b2 | C2/c | P4$_2$/mbc |
| crystal habit | hexagons | plates | — | crosses | — |
| a (Å) | 8.4520(10) | 8.90060(10) | 6.8208 | 9.9583(3) | 7.8554 |
| b (Å) | 8.4520(10) | 16.8152(2) | 6.8208 | 10.4988(3) | 7.8554 |
| c (Å) | 20.621(11) | 14.3808(2) | 8.4487 | 15.7961(4) | 17.0937 |
| α (deg) | 90 | 90 | 90 | 90 | 90 |
| β (deg) | 90 | 100.6000(10) | 90 | 98.407(2) | 90 |
| γ (deg) | 120 | 90 | 90 | 90 | 90 |
| V (Å$^3$) | 1275.8(7) | 2115.58(5) | 393.03 | 1633.74(8) | 1054.81 |
| Z | 6 | 8 | 2 | 8 | 4 |
| T (K) | 293 | 293 | 293 | 293 | 293 |
| $\rho_{calcd}$ (g cm$^{-3}$) | 4.400 | 3.537 | 4.760 | 4.581 | 3.724 |
| μ (mm$^{-1}$) | 37.146 | 29.868 | 40.193 | 38.677 | 29.967 |
| R [I$_o$ ≧ 2.50σ(I$_o$)][c] | 0.0459 | 0.0429 | 0.0082 | 0.0338 | 0.0366 |
| R$_w$ [I$_o$ ≧ 2.50σ(I$_o$)][c] | 0.0616 | 0.0564 | 0.0117 | 0.0543 | 0.0691 |
| goodness of fit | — | 1.1438 | — | 1.2462 | — |

[a]From ref 50,
[b]From X-ray powder diffraction data,
[c]The function minimized was $\Sigma w(|F_o| - |F_c|)^2$, where $w^{-1} = [\sigma^2(F_o) + (nF_o)^2]$ with n = 0 for β, 0.030 for δ, and 0 for γ and {Zn(NH$_3$)$_2$[Au(CN)$_2$]$_2$}, R = Σ||F$_o$| − |F$_c$||/Σ|F$_o$|; R$_w$ = [Σw(|F$_o$| − |F$_c$|)$^2$/Σw|F$_o$|$^2$]$^{1/2}$.

TABLE 10

Bond Lengths (Å) and Angles (deg) for 13β[a]

| | | | |
|---|---|---|---|
| Zn(1)—N(11) | 1.957(14) | Zn(1)—N(21) | 1.944(15) |
| Zn(1)—N(22) | 1.955(14) | Zn(1)—N(31) | 1.964(13) |
| Au(1)—Au(2*) | 3.2702(6) | Au(1)—Au(2†) | 3.2702(6) |
| Au(2')—Au(3) | 3.1925(7) | Au(2")—Au(3) | 3.1925(7) |
| Au(2")—Au(2†) | 3.1466(11) | | |
| Zn(1)—N(11)—C(11) | 168.6(16) | Zn(1)—N(21)—C(21) | 171.5(13) |
| Zn(1)—N(22)—C(22) | 162.9(14) | Zn(1)—N(31)—C(31) | 166.6(14) |
| N(11)—Zn(1)—N(21) | 111.4(6) | N(11)—Zn(1)—N(22) | 106.4(6) |
| N(11)—Zn(1)—N(31) | 106.3(6) | N(21)—Zn(1)—N(22) | 112.8(6) |
| N(21)—Zn(1)—N(31) | 108.9(6) | N(22)—Zn(1)—N(31) | 110.8(6) |
| Au(2*)—Au(1)—Au(2†) | 180.00 | Au(3‡)—Au(2†)—Au(1) | 104.944(17) |
| Au(3)—Au(2")—Au(2†) | 145.15(3) | Au(1)—Au(2†)—Au(2") | 109.35(2) |
| Au(2')—Au(3)—Au(2") | 141.53(4) | | |

[a]Symmetry operations:
*x + ½, y + ½, z;
'−x + 1, −y + 1, −z;
†−x + 2, −y + 1, −z;
‡x + 1 y, z;
"x, −y + 1, z − ½.

TABLE 11

Bond Lengths (Å) and Angles (deg) for 13δ[a]

| | | | |
|---|---|---|---|
| Zn(1)—N(11) | 1.975(10) | Zn(1)—N(21) | 1.956(10) |
| Zn(1)—N(31) | 1.968(10) | Zn(1)—N(32) | 1.956(10) |
| Au(1)—Au(3') | 3.3382(5) | Au(1)—Au(3") | 3.3382(5) |

TABLE 11-continued

Bond Lengths (Å) and Angles (deg) for 13δ[a]

| Au(2*)—Au(3″) | 3.3318(4) | Au(2*)—Au(3) | 3.3318(4) |
|---|---|---|---|
| N(11)—Zn(1)—N(32) | 110.3(4) | N(11)—Zn(1)—N(21) | 113.8(4) |
| N(11)—Zn(1)—N(31) | 100.6(4) | N(21)—Zn(1)—N(31) | 118.9(4) |
| N(21)—Zn(1)—N(32) | 101.2(4) | N(31)—Zn(1)—N(33) | 112.3(5) |
| Zn(1)—N(11)—C(11) | 161.8(10) | Zn(1)—N(21)—C(21) | 163.1(10) |
| Zn(1)—N(31)—C(31) | 158.7(10) | Zn(1)—N(32)—C(32) | 159.3(10) |
| Au(3′)—Au(1)—Au(3″) | 180.00 | Au(3)—Au(2*)—Au(3″) | 180.00 |
| Au(1)—Au(3″)—Au(2*) | 65.690(8) | | |

[a]Symmetry operations:
'x ½, y + ½, z;
″-x + ½, -y + 3/2, -z + 1;
*x, -y + 2, z + ½.

TABLE 12

Summary of Luminescence data for 13α-13δ,
[Zn(NH$_3$)$_4$][Au(CN)$_2$]$_2$ 15, and {Zn(NH$_3$)$_2$[Au(CN)$_2$]$_2$} 14

| compound | emission maximum (nm) | excitation maximum (nm) |
|---|---|---|
| α | 390, 480 | 345 |
| β | 450 | 390 |
| γ | 440 | 360 |
| δ | none | none |
| [Zn(NH$_3$)$_4$][Au(CN)$_2$]$_2$ | 430 | 365 |
| {Zn(NH$_3$)$_2$[Au(CN)$_2$]$_2$} | 500 | 400 |

REFERENCES (1) Janiak, C. *J. Chem. Soc. Dalton Trans.* 2003, 2781-2804.
(2) James, S. L. *Chem. Soc. Rev.* 2003, 32, 276-288.
(3) White-Morris, R. L.; Olmstead, M. M.; Jiang, F.; Tinti, D. S.; Balch, A. L. *J. Am. Chem. Soc.* 2002, 124, 2327-2336.
(4) Mansour, M. A.; Connick, W. B.; Lachicotte, R. J.; Gysling, H. J.; Eisenberg, R. *J. Am. Chem. Soc.* 1998, 120, 1329-1330.
(5) Rawashdeh-Omary, M. A.; Omary, M. A.; Fackler, J. P., Jr.; Galassi, R.; Pietroni, B. R.; Burini, A. *J. Am. Chem. Soc.* 2001, 123, 9689-9691.
(6) Fernandez Eduardo, J.; Lopez-De-Luzuriaga Jose, M.; Monge, M.; Olmos, M. E.; Perez, J.; Laguna, A.; Mohamed Ahmed, A.; Fackler John, P., Jr. *J. Am. Chem. Soc.* 2003, 125, 2022-2023.
(7) Exstrom, C. L.; Sowa, J. R., Jr.; Daws, C. A.; Janzen, D.; Mann, K. R.; Moore, G. A.; Stewart, F. F. *Chem. Mater.* 1995, 7, 15-17.
(8) Drew, S. M.; Janzen, D. E.; Buss, C. E.; MacEwan, D. I.; Dublin, K. M.; Mann, K. R. *J. Am. Chem. Soc.* 2001, 123, 8414-8415.
(9) Beauvais, L. G.; Shores, M. P.; Long, J. R. *J. Am. Chem. Soc.* 2000, 122, 2763-2772.
(10) Buss, C. E.; Anderson, C. E.; Pomije, M. K.; Lutz, C. M.; Britton, D.; Mann, K. R. *J. Am. Chem. Soc.* 1998, 120, 7783-7790.
(11) Bariain, C; Matias, I. R.; Romeo, I.; Garrido, J.; Laguna, M. *Appl. Phys. Lett.* 2000, 77, 2274-2276.
(12) Kunugi, Y.; Mann, K. R.; Miller, L. L.; Exstrom, C. L. *J. Am. Chem. Soc.* 1998, 120, 589-590.
(13) Kunugi, Y.; Miller, L. L.; Mann, K. R.; Pomije, M. K. *Chem. Mater.* 1998, 10, 1487-1489.
(14) Daws, C. A.; Exstrom, C. L.; Sowa, J. R., Jr.; Mann, K. R. *Chem. Mater.* 1997, 9, 363-368.
(15) Exstrom, C. L.; Pomije, M. K.; Mann, K. R. *Chem. Mater.* 1998, 10, 942-945.
(16) Dong, W.; Zhu, L.-N.; Sun, Y.-Q.; Liang, M.; Liu, Z.-Q.; Liao, D.-Z.; Jiang, Z.-H.; Yan, S.-P.; Cheng, P. *Chem. Commun.* 2003, 2544-2545.
(17) Abrahams, S. C.; Zyontz, L. E.; Bernstein, J. L. *J. Chem. Phys.* 1982, 76, 5458.
(18) Abrahams, S. C.; Bernstein, J. L.; Liminga, R.; Eisenmann, E. T. *J. Chem. Phys.* 1980, 73, 4585.
(19) Colacio, E.; Lloret, F.; Kivekaes, R.; Ruiz, J.; Suarez-Varela, J.; Sundberg, M. R. *Chem. Commun.* 2002, 592-593.
(20) Hoskins, B. F.; Robson, R.; Scarlett, N. V. Y. *Angew. Chem. Int. Ed. Engl.* 1995, 54, 1203.
(21) Assefa, Z.; Shankle, G.; Patterson, H. H.; Reynolds, R. *Inorg. Chem.* 1994, 33, 2187-2195.
(22) Stier, A.; Range, K.-J. *Z. Naturforsch.* 1996, 51b, 698.
(23) Stier, A.; Range, K.-J. *Z. Kristallgr.* 1997, 212, 51.
(24) Assefa, Z.; Staples, R. J.; Fackler, J. P., Jr.; Patterson, H. H.; Shankle, G. *Acta Crystallogr.* 1995, C51, 2527.
(25) Leznoff, D. B.; Xue, B.-Y.; Patrick, B. O.; Sanchez, V.; Thompson, R. C. *Chem. Commun.* 2001, 259-260.
(26) Leznoff, D. B.; Xue, B. Y.; Stevens, C. L.; Storr, A.; Thompson, R. C.; Patrick, B. O. *Polyhedron* 2001, 20, 1247-1254.
(27) Leznoff, D. B.; Xue, B.-Y.; Batchelor, R. J.; Einstein, F. W. B.; Patrick, B. O. *Inorg. Chem.* 2001, 40, 6026-6034.
(28) Shorrock, C. J.; Xue, B.-Y.; Kim, P. B.; Batchelor, R. J.; Patrick, B. O.; Leznoff, D. B. *Inorg. Chem.*, 2002, 41, 6743-53.
(29) Leznoff, D. B.; Draper. N. D.; Batchelor. R. J. *Polyhedron.* 2003, 22, 1735-1743.
(30) Draper, N. D.; Batchelor, R. J.; Sih, B. C.; Ye, Z.-G.; Leznoff, D. B. *Chem. Mater.,* 2003, 15, 1612-1616.
(31) Shorrock, C. J.; Jong, H.; Batchelor, R. J.; Leznoff, D. B. *Inorg. Chem.,* 2003, 42, 3917-3924.
(32) Draper, N. D.; Batchelor, R. J.; Leznoff, D. B. *Crystal Growth and Design.* 2004, 4, 621-632.
(33) Draper, N. D.; Batchelor, R. J.; Aguiar, P. M.; Kroeker, S.; Leznoff, D. B. *Inorg. Chem.,* 2004, 43, 6557-6567.
(34) Lefebvre, J.; Batchelor, R. J.; Leznoff, D. B. *J. Am. Chem. Soc.* 2004, 126, 16117-16125.
(35) Katz, M. J.; Batchelor, R. J.; Leznoff, D. B., *J. Am. Chem. Soc., in press.*
(36) Kahn, O. *Molecular Magnetism*; VCH: Weinheim. 1993.
(37) Gabe, E. J.; White, P. S.; Enright, G. D. *DIFRAC A Fortran 77 Control Routine for 4-Circle Diffractometers*: N. R. C: Ottawa. 1995.
(38) Gabe, E. J.; LePage, Y.; Charland, J.-P.; Lee, F. L.; White, P. S., *J. Appl. Crystallogr.* 1989, 22, 384.
(39) Higashi, T. *Program for Absorption Correction*; Rigaku Corporation; Tokyo. Japan. 1999.

(40) Watkin, D. J.; Prout, C. K.; Carruthers, J. R.; Betteridge, P. W.; Cooper, R. I. *CRYSTALS Issue 11* Chemical Crystallography Laboratory. University of Oxford, Oxford, England, 1999.
(41) Farrugia, L. J. *J. Appl. Crystallogr.* 1997, 30, 565.
(42) Fenn, T. D.; Ringe, D.; Petsko, *J. Appl. Crystallogr.* 2003, 36, 944-947. (Persistence of Vision Raytracing: http://www.povray.org).
(43) Dunbar, K. R.; Heintz, R. A. *Prog. Inorg Chem.* 1997, 45, 283-391.
(44) Addison, A. W.; Rao, T. N.; Reedijk, J.; Van Rijn, J.; Verschoor, G. C. *J. Chem. Soc., Dalton Trans.* 1984, 1349-1356.
(45) Schmidbaur, H. *Chem. Soc. Rev.* 1995, 24, 391.
(46) Carlin, R. L. *Magnetochemistiy*; Springer-Verlag; Berlin, Heidelberg, German), 1986.
(47) Colacio, E.; Lloret, F.; Kivekaes, R.; Suarez-Varela, J.; Sundberg, M. R.; Uggla, R. *Inorg. Chem.* 2003, 42, 560-565.
(48) Chomic, J.; Cernak, J. *Thermochim. Acta* 1985, 93, 93.
(49) Noro, S.-i.; Kitaura, R.; Kondo., M.; Kitagawa, S.; Ishii, T.; Matsuzaka, H.; Yamashita, M., *J. Am. Chem. Soc.* 2002, 124, 2568-2583.
(50) Seki, K. *Chem. Commun.* 2001, 1496-1497.
(51) Uemura, K.; Kitagawa, S.; Kondo, M.; Fukui, K.; Kitaura, R.; Chang, H.-C; Mizutani, T. *Chem. Eur. J.* 2002, 8, 3586-3600.
(52) Eddaoudi, M.; Moler, D. B.; Li, H.; Chen, B.; Reineke, T. M.; O'Keeffe, M.; Yaghi, O. M. *Acc. Chem. Res.* 2001, 34, 319-330.
(53) Moulton, B.; Zaworotko, M. J. *Chem. Rev.* 2001, 101, 1629-1658.
(54) Batten, S. R.; Murray, K. S. *Aust. J. Chem.* 2001, 54, 605-609.
(55) Dunitz, J. D.; Bernstein, *J. Acc. Chem. Res.* 1995, 28, 193.
(56) Bernstein, J. *Polymorphism in Molecular Crystals*; Oxford University Press; Oxford, 2002.
(57) Braga, D.; Grepioni, F. *Chem. Soc. Rev.* 2000, 29, 229-238.
(58) Bernstein, J.; Dave, R. J.; Henck, J.-O. *Angew. Chem., Int. Ed.* 1999, 38, 3440.
(59) Jensen, P.; Batten, S. R.; Fallon, G. D.; Hockless, D. C. R.; Moubaraki, B.; Murray, K. S.; Robson, R., *J. Solid State Chem.* 1999, 145, 387-393.
(60) Barnett, S. A.; Blake, A. J.; Champness, N. R.; Wilson, C. *Chem. Commun.* 2002, 1640-1641.
(61) Heintz. R. A.; Zhao. H.; Ouyang. X.; Grandinetti. G.; Cowen. J.; Dunbar. K. R. *Inorg. Chem.* 1999, 38, 144.
(62) Atwood, J. L.; Barbour, L. J.; Jerga, A.; Schottel, B. L. *Science* 2002, 298, 1000-1002.
(63) Cote, A. P.; Shimizu, G. K. H. *Chem. Commun.* 2001, 251-252.
(64) Edgar, M.; Mitchell, R.; Slawin, A. M.; Lightfoot, P.; Wright, P. A. *Chem. Eur. J.* 2001, 7, 5168-5175.
(65) Miller, P. W.; Nieuwenhuyzen, M.; Xu, X.; James, S. L. *Chem. Commun.* 2002, 2008-2009.
(66) Lozano, E.; Nieuwenhuyzen, M.; James, S. L. *Chem. Eur. J.* 2001, 7, 2644-2651.
(67) Kitaura, R.; Fujimoto, K.; Noro, S.-i.; Kondo, M.; Kitagawa, S. *Angew. Chem., Int. Ed.* 2002, 41, 133-135.
(68) Côté, A. P.; Ferguson, M. J.; Khan, K. A.; Enright, G. D.; Kulynych, A. D.; Dalrymple, S. A.; Shimizu, G. K. H. *Inorg. Chem.* 2002, 41, 287-292.
(69) Lefebvre, J.; Chartrand, D.; Leznoff, D. B., *Polyhedron* 2007, 26, 2189.
(70) Betteridge, P. W.; Carruthers, J. R.; Cooper, R. I.; Prout, K.; Watkin, D. J., 2003 36, 1487.
(71) Watkin, D. J.; Prout, C. K.; Pearce, L. J., *Cameron*; University of Oxford Chemical Crystallography Laboratory; Oxford, U.K., 1996.
(72) Boultif, A.; Louer, D., *J. Appl. Cryst.* 2004, 37, 724.
(73) Kraus, W.; Nolze, G., *J. Appl. Crystallogr.* 1996, 29, 301.
(74) Soma, T.; Iwamoto, T., *Chem. Lett.* 1995, 271.
(75) Parmar, M. M.; Khan, O.; Ford, J. L., *Cryst. Growth Des.* 2007, 7, 1635.
(76) Blagus, A.; Kaitner, B., *J. Chem. Crystallogr.* 2007, 37, 473.
(77) Katz, M. J.; Shorrock, C. J.; Batchelor, R. J.; Leznoff, D. B., *Inorg. Chem.* 2006, 45, 1757.
(78) Blake, A. J.; Brooks, N. R.; Champness, N. R.; Crew, M.; Deveson, A.; Fenske, D.; Gregory, D. H.; Hanton, L. R.; Hubberstey, P.; Schröder, M., *Chem. Commun.* 2001, 1432.
(79) Lu, J.; Wang, X.-J.; Yang, X.; Ching, C.-B., *Cryst. Growth Des.* 2007, 7, 1590.
(80) Lee, I. S.; Kim, K. T.; Lee, A. Y.; Myerson, A. S., *Cryst. Growth Des.* 2008, 8, 108.
(81) Molgaard, A.; Larsen, S., *Acta Cryst.* 2004, D60, 472.
(82) Zaworotko, M. J., *Chem. Soc. Rev.* 1994, 23, 283.
(83) Sun, J.; Weng, L.; Zhou, Y.; Chen, J.; Chen, Z.; Liu, Z.; Zhao, D., *Angew. Chem. Int. Ed.* 2002, 41, 4471.
(84) Hu, S.; Tong, M.-L., *Dalton Trans.* 2005, 1165.
(85) Batten, S. R.; Robson, R., *Angew. Chem. Int. Ed.* 1998, 37, 1460.
(86) Öhrström, L.; Larsson, K., *Molecule-Based Materials: The Structural Network Approach*, Elsevier; Amsterdam. 2005.
(87) Wenk, H.-R.; Bulakh, A., *Minerals: Their Constitution and Origin*. Cambridge University Press; Cambridge, 2004.
(88) Moulton, B.; Zaworotko, M. J., *Chem. Rev.* 2001, 101, 1629.
(89) Blatov, V. A.; Carlucci, L.; Ciani, G.; Proserpio, D. M., *Cryst Eng Comm* 2004, 6, 377.
(90) Proserpio, D. M.; Hoffmann, R.; Preuss, P., *J Am. Chem. Soc.* 1994, 116, 9634.
(91) Feldtmann, W. B., *J. Chem. Metall. Min. Soc. South Afr.* 1919, 20, 13.
(92) Dunitz, J. D.; Bernstein, J., *Acc. Chem. Res.* 1995, 28, 193.
(93) Blagden, N.; Davey, R. J., *Cryst. Growth Des.* 2003, 3, 873.
(94) Gavezzotti, A., *Cryst Eng Comm.* 2002, 4, 343.
(95) Buschmann, W. E.; Miller, J. S., *Inorg. Chem. Commun.* 1998, 1, 174.
(96) Cartraud, P.; Cointot, A.; Renaud, A. J., *J. Chem. Soc. Faraday Trans.* 1981, 77, 1561.
(97) Evans, O. R.; Lin, W., *Acc. Chem. Res.* 2002, 35, 511.
(98) Bondi, A., *J. Phys. Chem.* 1964, 68, 441.
(99) Bardaji, M.; Laguna, A., *J. Chem. Educ.* 1999, 76, 201.
(100) Stender, M.; Gimstead, M. M.; Balch, A. L.; Rios, D.; Attar, S., *Dalton Trans.* 2003, 4282.
(101) Pham, D. M.; Rios, D.; Olmstead, M. M.; Balch, A. L., *Inorg. Chim. Acta* 2005, 358, 4261.
(102) Fackler, J., J. P., *Inorg. Chem.* 2002, 41, 6959.
(103) Rawashdeh-Omary, M. A.; Omary, M. A.; Patterson, H. H.; Fackler Jr., J. P., *J. Am. Chem. Soc.* 2001, 123, 11237.
(104) Hettiarachchi, S. R.; Schaefer, B. K.; Yson, R. L.; Staples, R. J.; Herbst-Irmer, R.; Patterson, H. H., *Inorg. Chem.* 2007, 46, 6997.
(105) Arvapally, R. K.; Sinha, P.; Hettiarachchi, S. R.; Coker, N. L.; Bedel, C. E.; Patterson, H. H.; Elder, R. C: Wilson, A. K.; Omary, M. A., *J. Phys. Chem. C* 2007, 111, 10689.

(106) Stender, M.; White-Morris, R. L.; Olmstead, M. M.; Balch, A. L., *Inorg Chem.* 2003, 42, 4504.
(107) Timmer, B.; Olthuis, W.; van den Berg, A., *Sens. Actuators B* 2005, 107, 666.
(108) Budavari, S.; O'Neil, M. J.; Smith, A.; Heckelman, P. E.; Kinneary, J. F., *The Merck Index: An Encyclopedia of Chemicals, Drugs, and Biologicals*, Merck; New Jersey, 1996.
(109) Nakamoto, K., *Infrared and Raman Spectra of Inorganic and Coordination Compounds*, Wiley; New York. 1986.
(110) Migdal-Mikuli, A.; Mikuli, E.; Hetmanczyk, L.; Natkaniec, I.; Holderna-Natkaniec, K.; Lasocha, W., *J Solid State Chem.* 2003, 174, 357.
(111) Hillebrecht, H.; Thiele, G.; Koppenhöfer, A.; Vahrenkamp, H., *Z. Naturforsch., B* 1994, 49, 1163.
(112) Prince, R. H. In *Comprehensive Coordination Chemistry*; Oxford, 1987; Pergamon; Oxford, 1987.
(113) Suárez-Varela, J.; Sakiyama, H.; Cano, J.; Colacio, E., *Dalton Trans.* 2007, 249.
(114) Vlcek, A.; Orendác, M.; Orendácová, A.; Kajnaková, M.; Papageorgiou. T.; Chomic, J.; Černák, J.; Massa, W.; Feher, A., *Sol. State Sci.* 2007, 9, 116.
(115) Reller, A.; Oswald, H.-R., *J. Therm. Anal.* 1994, 41, 535.
(116) Kaneko, W.; Ohba, M.; Kitagawa, S., *J. Am. Chem. Soc.* 2007, 129, 13706.
(117) Kitagawa, S.; Kitaura, R.; Noro, S.-I.; *Angew. Chem. Int. Ed.* 2004, 43, 2334.
(118) Cole, S. C,; Coles, M. P.; Coles, P. B., *Dalton Trans.* 2003, 3663.
(119) Rout, C. S.; Hegde, M.; Govindaraj, A.; Rao, C. N. R., *Nanotechnohgy* 2007, 18, 205504.
(120) Galbarra, D.; Arregui, F. J.; Matias, I. R.; Claus, R. O., *Smart Mater. Struct.* 2005, 14, 739.
(121) Thangadurai, V.; Weppner, W., *Solid State Ionics* 2004, 174, 175.
(122) Vidotti, M.; Dall'Antonia, L. H.; Cintra, E. P.; Córdoba de Torresi, S. I., *Electrochem. Acta* 2004, 49, 3665.
(123) Lee, Y.-S.; Song, K.-D.; Huh, J.-S.; Chung, W.-Y.; Lee, D.-D., *Sens. Actuators B* 2005, 108, 292.
(124) Yagi, T.; Kuboki, N.; Suzuki, Y.; Uchino, N.; Nakamura, K.; Yoshida, K., *Opt. Rev.* 1997, 4, 596.
(125) Malins, C.; Doyle, A.; MacCraith, B. D.; Kvasnik, F.; Landl, M.; Simon, P.; Kalvoda, L.; Lukas, R.; Pufler, K.; Babusik, I., *J. Environ. Monit.* 1999, 1, 417.
(126) Katz, M. J.; Aguiar, P. M.; Batchelor, R. J.; Bokov, A. A.; Ye, Z.-G.; Kroeker, S.; Leznoff, D. B., *J. Am. Chem. Soc.* 2006, 128, 3669.

What is claimed is:

1. A method of detecting an analyte comprising:
(a) providing a sensor comprising a coordination polymer having the chemical formula:

$$M_W[M'_X(Z)_Y]_N$$

wherein M and M' are the same or different metals capable of forming a coordination complex with the Z moiety, wherein at least one of the Z moiety comprises a bridging unit bound to M by a coordinate bond;
Z is selected from the group consisting of halides, pseudohalides, thiolates, alkoxides and amides
W is between 1-6;
X and Y between 1-9; and
N is between 1-5;
(b) exposing said polymer to a supply of said analyte, wherein said analyte is selected from the group consisting of ammonia and amines; and
(c) detecting any chromatic changes in said polymer resulting from exposure to said analyte.

2. The method as defined in claim 1, wherein said analyte is ammonia.

3. The method as defined in claim 1, wherein said polymer comprises $Zn[Au(CN)_2]_2$ in any of its polymorphic forms.

4. The method as defined in claim 1, wherein said polymer comprises $Cu[Au(CN)_2]_2$.

5. The method as defined in claim 1, wherein M is Cu or Zn, M' is Au, Z is CN, W is 1 and X is 1 and Y is 2.

6. The method as defined in claim 1, wherein said detecting comprises sensing any changes in luminescence of said polymer.

7. The method as defined in claim 1, wherein said detecting comprises sensing any changes in colour of said polymer.

8. The method as defined in claim 1, wherein said detecting comprises spectroscopically identifying any changes in the infrared signature of said polymer.

9. The method as defined in claim 2, wherein said exposing comprises exposing said polymer to ammonia present in the breath of a patient.

10. The method as defined in claim 3, wherein said polymer comprises $Zn[Au(CN)_2]_2$ in its β polymorphic form.

11. The method as defined in claim 1, wherein said detecting comprises detecting binding of said analyte to M.

12. The method as defined in claim 1, wherein said detecting comprises detecting a change in binding of said bridging unit to M.

13. The method as defined in claim 12, wherein said detecting comprises detecting a change in the distance between units of M' in said coordination complex.

14. A method of detecting an analyte comprising:
(a) providing a sensor comprising a vapochromic coordination polymer having the formula:

$$M_W[M'_X(Z)_Y]_N$$

wherein M is Cu or Zn, M' is Au or Ag, Z is selected from the group consisting of CN, SCN, SeCN, TeCN, OCN, CNO and NNN, W is 1, X is 1, Y is 2 and N is 2, wherein at least one of the Z moiety comprises a bridging unit bound to M by a coordinate bond;
(b) exposing said sensor to a supply of said analyte, wherein said analyte is selected from the group consisting of ammonia and amines; and
(c) detecting chromatic changes in said polymer resulting from exposure to said analyte.

15. The method as defined in claim 14, wherein Z is CN.

16. The method as defined in claim 14, wherein said detecting comprises detecting a change in binding of said bridging unit to M resulting from binding of said analyte to M.

17. The method as defined in claim 15, wherein said detecting chromatic changes comprises detecting both a visible change in colour of said polymer and a non-visible change in the $\upsilon_{CN}$ infra-red signature of said polymer.

18. The method as defined in claim 14, wherein said analyte is ammonia and wherein said sensor is configured to vapochromically detect said ammonia at concentrations less than 50 parts per million.

19. The method as defined in claim 18, wherein said sensor is configured to vapochromically detect said ammonia at concentrations less than 10 parts per million.

20. The method as defined in claim 19, wherein said detecting occurs less than 20 seconds after said exposing.

21. The method as defined in claim 14, wherein said analyte is a primary amine or a secondary amine.

22. The method as defined in claim 21, wherein said sensor is configured to vapochromically detect said analyte at concentrations less than 10 parts per million.

23. The method as defined in claim 3, wherein said polymer comprises $Zn[Au(CN)_2]_2$ in its α polymorphic form.

24. The method as defined in claim 3, wherein said polymer comprises $Zn[Au(CN)_2]_2$ in its δ polymorphic form.

25. The method as defined in claim 3, wherein said polymer comprises $Zn[Au(CN)_2]_2$ in its γ polymorphic form.

\* \* \* \* \*